United States Patent [19]
Pinol et al.

[11] Patent Number: 5,393,758
[45] Date of Patent: Feb. 28, 1995

[54] SUBSTITUTED AZETIDINYLPYRIDONE NAPHTHYRIDINE CARBOXYLIC ACID DERIVATIVES AND THEIR APPLICATION AS MEDICAL PRODUCTS

[75] Inventors: Augusto C. Pinol; Jordi F. Constansa; Juan P. Corominas, all of Barcelona, Spain

[73] Assignee: Laboratorios Del Dr. Esteve S.A., Barcelona, Spain

[21] Appl. No.: 191,153

[22] Filed: Feb. 3, 1994

Related U.S. Application Data

[60] Continuation of Ser. No. 855,215, Mar. 20, 1992, abandoned, which is a division of Ser. No. 762,035, Sep. 11, 1991, abandoned, which is a continuation of Ser. No. 494,222, Mar. 15, 1990, abandoned.

[30] Foreign Application Priority Data

Jan. 29, 1989 [FR] France .................. 89 08695
Mar. 16, 1989 [FR] France .................. 89 03459
Nov. 20, 1989 [FR] France .................. 89 15178

[51] Int. Cl.$^6$ .................. A61K 31/435; C07D 471/04
[52] U.S. Cl. .................. 514/300; 546/123
[58] Field of Search .................. 546/123, 156; 514/300

[56] References Cited

U.S. PATENT DOCUMENTS 4,777,175 10/1988 Culbertson et al. .................. 546/123
4,997,943 3/1991 Iwata et al. .................. 546/156
5,039,683 8/1991 Nakanishi .................. 546/156

FOREIGN PATENT DOCUMENTS 60-89480 5/1985 Japan .
60-126284 7/1985 Japan .
61-137885 6/1986 Japan .

OTHER PUBLICATIONS

Egawa et al., J. Med. Chem. v. 27, pp. 1543-48 (1984).

*Primary Examiner*—Bernard Dentz
*Attorney, Agent, or Firm*—Dressler, Goldsmith, Shore & Milnamow Ltd.

[57] ABSTRACT

The present invention relates to new azetidine derivatives of substituted azetidinylpyridonecarboxylic acids, of 1,4-dihydro-4-oxo-3-quinolinecarboxylic, 4-oxo-1,8-naphthyridine-3-carboxylic and 2,3-dihydro-7-oxo-7H-pyrido[1,2,3-de][1,4]benzoxazine-6-carboxylic acids, represented by the general formula I:

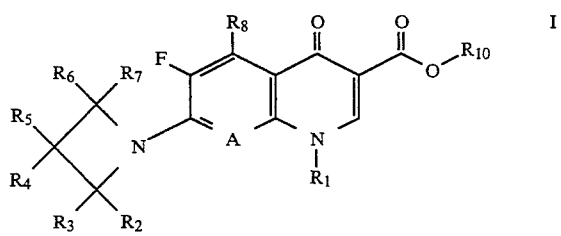

The present invention also relates to therapeutically acceptable salts of these compounds, a process for preparing them and their application as medicinal products.

7 Claims, No Drawings

SUBSTITUTED AZETIDINYLPYRIDONE NAPHTHYRIDINE CARBOXYLIC ACID DERIVATIVES AND THEIR APPLICATION AS MEDICAL PRODUCTS

This application is a continuation of application Ser. No. 07/855,215, filed Mar. 20, 1992, now abandoned, which is a division of Ser. No. 07/762,035, filed Sep. 11, 1991, now abandoned, which is a continuation of Ser. No. 07/494,222, filed Mar. 15, 1990, now abandoned.

The present invention relates to new azetidine derivatives of pyridonecarboxylic acids, 1,4-dihydro-4-oxo-3-quinolinecarboxylic, 4-oxo-1,8-naphthyridine-3-carboxylic and 2,3-dihydro-7-oxo-7H-pyrido[1,2,3-de][1,4-]benzoxazine-6-carboxylic acids, therapeutically acceptable salts of these compounds, a process for preparing them and also their application as medicinal products.

The compounds which are the subject of the present invention may be used in the pharmaceutical industry as intermediates, and for the preparation of medicinal products.

Some 3-monosubstituted azetidines attached to the 7-position of some quinolones and naphthyridines are described in the patents Eur. Pat. Appl. EP 106,489, Eur. Pat. Appl. EP 153,163, Japan Kokkai JP 58/72,589 (83/72,589), Japan Kokkai JP 60/89,840 (85/89,840) and Japan Kokkai JP 60/126,284 (85/12,684).

Some azetidines mono- or disubstituted in their 3-position and which are attached to the 7-position of some quinolones and pyridobenzoxazines are described in French Patent Application 87/18,289 and its Addition 88/09,816.

We have now discovered that the new azetidine derivatives of 1,4-dihydro-4-oxo-3-quinolinecarboxylic, 4-oxo-1,8-naphthyridine-3-carboxylic and 2,3-dihydro-7-oxo-7H-pyrido[1,2,3-de][1,4]benzoxazine-6-carboxylic acids which form the subject of the present invention possess very good antimicrobial activity.

The compounds which are the subject of the present invention correspond to the general formula I

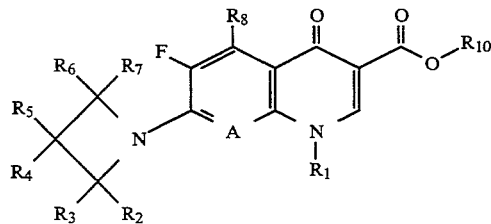

in which A represents a nitrogen atom, or alternatively a carbon atom with a hydrogen atom attached (C—H), or alternatively a carbon atom with a halogen attached (C—X) and in this case X represents a chlorine, fluorine or bromine atom, or alternatively a carbon atom with a hydroxyl radical (C—OH);

$R_1$ represents a lower alkyl or cycloalkyl radical, a lower haloalkyl radical, an aryl radical or an aryl radical substituted, in particular, with one or more fluorine atom(s);

$R_2$ and $R_7$, which may be the same or different, represent a hydrogen atom or a lower alkyl radical;

$R_3$, $R_5$ and $R_6$, which may be the same or different, represent a hydrogen atom, a lower alkyl radical, an aminoalkyl radical, an alkylamino radical or an alkylaminoalkyl radical;

$R_4$ represents a hydrogen atom, a lower alkyl radical, a hydroxyl radical, an amino radical, an aminoalkyl radical, an alkylamino radical, a dialkylamino radical, a nitrogenous heterocyclic radical, preferably aromatic, which can be three- to six-membered ring, an alkylaminoalkyl radical, an alkylcarboxamido radical and, in this latter case, it being possible for the alkyl radical to be substituted with one or more halogens, an arylsulphonyloxy radical, an alkylsulphonyloxy radical, a carboxamido radical which can be substituted or unsubstituted on the nitrogen, or a cyano radical;

$R_8$ represents a hydrogen atom, a nitro radical or an amino or substituted amino radical;

A and $R_1$ together can form a link represented by a group C—CH$_2$—CH$_2$—CHR$_9$— or C—O—CH$_2$—CHR$_9$— in which $R_9$ represents a hydrogen atom or a lower alkyl radical and, in this latter case, there is a chiral centre with an "R" or "S" configuration;

$R_{10}$ represents a hydrogen atom or a $C_1$ to $C_4$ lower alkyl radical;

the azetidine substituents can have, depending on the number, nature and relative position of the substituents, up to three chiral centres, each of them with an "R" or "S" configuration; as well as their physiologically acceptable salts with inorganic acids, such as the hydrochlorides, or with organic acids, such as the toluenesulphonates or methylsulphonates.

The stereochemistry of the products which are the subject of the present invention is determined by that of the starting materials. By selection of the stereoisomerism of each of the starting materials, all the possible stereoisomers can be obtained, and in the case where the reaction product is a mixture of stereoisomers, the components may be separated and their configuration established by well-known methods.

The new derivatives of general formula I may be prepared, according to the invention, according to the following method:

By the reaction of a compound of general formula II

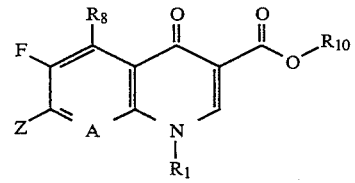

in which A, $R_1$, $R_8$ and $R_{10}$ have the meanings stated above and Z represents a halogen atom, preferably a chlorine or a fluorine, with an azetidine of general formula III

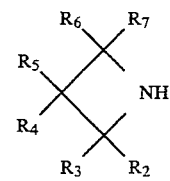

in which $R_2$, $R_3$, $R_4$, $R_5$, $R_6$ and $R_7$ have the meanings stated above.

The heterocyclic compounds of general formula II which can be used as starting materials for preparing the compounds of the invention are compounds described, for example in H. Koga, A. Itoh, S. Murayama, S. Suzue and T. Irikura *J. Med. Chem.*, 1980, 23, 1358, or alternatively in H. Egawa, T. Miyamoto, A. Minamida, Y. Nishimura, H. Okada, H. Uno and J. Matsumoto, *J. Med. Chem.*, 1984, 27, 1543.

Furthermore, the compounds of general formula III, which constitute the other starting materials for the preparation of the compounds of the invention according to the general formula I, are known or else are synthesized as, for example, in A. G. Anderson and R. Lok, *J. Org. Chem.* 1972, 37, 3953, or alternatively in R. H. Higgins and N. H. Cromwell, *J. Heterocycl. Chem.*, 1971, 8, 1059 and also in N. H. Cromwell and B. Phillips, *Chem. Revs.* 1979, 79, 331.

The azetidines of general formula III can have, depending on the number, nature and relative position of the substituents, up to three chiral centres, and the different stereoisomers may be obtained either by asymmetric synthesis or by various types of separations, according to methods known in organic chemistry.

The reaction is performed in the presence of a suitable solvent, for example dimethyl sulphoxide, dimethylformamide, pyridine, trialkylamines such as triethylamine, methylene chloride or chloroform, or alternatively ethers such as tetrahydrofuran or dioxane, or mixtures of these solvents.

The most appropriate temperatures vary between room temperature and the refluxing temperature of the solvent, and the reaction time is between 1 hour and 24 hours.

In the examples which follow, the preparation of new derivatives according to the invention is described. Some ways of using them will also be described.

The examples below, given simply by way of illustration, are in no way, however, to limit the scope of the invention.

EXAMPLE 1

Preparation of 1-cyclopropyl-6-fluoro-7-(1-azetidinyl)-1,4-dihydro-4-oxo-3-quinolinecarboxylic acid A mixture of 0.6 g (2.2 mmol) of 1-cyclopropyl-6,7-difluoro-1,4-dihydro-4-oxo-3-quinolinecarboxylic acid, 0.25 g (4.4 mmol) of azetidine and 1 ml of triethylamine in 8 ml of pyridine is heated to 110° C. in a closed vessel for 2 hours. The mixture is allowed to cool and is filtered and the product is washed with water, ethanol and ether. 0.275 g of 1-cyclopropyl-6-fluoro-7-(1-azetidinyl)-1,4-dihydro-4-oxo-3-quinolinecarboxylic acid, melting point 291°-4° C., is thereby obtained.

Spectroscopic data: $^1$H NMR, $\delta$, J=Hz, [DMSO-TFAA]; 8.57 (s, 1H); 7.78 (d, J=13, 1H); 6.86 (d, J=8, 1H); 4.22 (t, J=7, 4H); 3.73 (m, 1H); 1.15 (m, 6H). IR(KBr).-1725, 1631, 1479, 1464, 1348 cm$^{-1}$.

EXAMPLE 2

Preparation of 1-cyclopropyl-6,8-difluoro-7-(3-methyl-3-methylamino-1-azetidinyl)-1,4-dihydro-4-oxo-3-quinolinecarboxylic acid A mixture of 1.35 g (4.8 mmol) of 1-cyclopropyl-6,7,8-trifluoro-1,4-dihydro-4-oxo-3-quinolinecarboxylic acid, 1.45 g (6.2 mmol) of 3-methyl-3-trifluoroacetamido-azetidine hydrochloride and 1 ml of triethylamine in 15 ml of pyridine is heated to reflux for 2 hours. The mixture is evaporated under vacuum, the residue is diluted with ice-cold water and filtered and the product is washed with water. 2.2 g of 1-cyclopropyl-6,8-difluoro-7-{3-methyl-3-[N-(methyl)trifluoroacetamido]-1-azetidinyl}-1,4-dihydro-4-oxo-3-quinolinecarboxylic acid, melting point 291°-4° C., are thereby obtained, which product is then hydrolysed by heating it in a mixture of 4 ml of 10% sodium hydroxide and 20 ml of water with 1 ml of ethanol for 1 hour. The mixture is filtered while hot, the filtrate is acidified with acetic acid, the resulting mixture is filtered and the product is washed with water. 1.57 g of 1-cyclopropyl-6,8-difluoro-7-(3-methyl-3-methylamino-1-azetidinyl)-1,4-dihydro-4-oxo-3-quinoline-carboxylic acid, melting point >300° C., are thereby obtained.

Spectroscopic data: $^1$H NMR, $\delta$,J=Hz, [DMSO-TFAA]; 1.1 (m, 4H); 1.65 (s, 3H); 2.7 (s, 3H); 4.0 (m, 1H); 4.5 (AB, J=7, 4H); 7.75 (d, J=, 1H); 8.6 (s, 1H); 9.4 (broad, 2H). IR(KBr).-2918, 1731, 1622, 1470, cm$^{-1}$.

EXAMPLE 3

Preparation of 1-cyclopropyl-6-fluoro-7-(3-methyl-3-methylamino-1-azetidinyl)-1,4-dihydro-4-oxo-3-quinolinecarboxylic acid By a procedure completely analogous to that of Example 2, 1-cyclopropyl-6-fluoro-7-{3-methyl-3-[N-(methyl)trifluoroacetamido]-1-azetidinyl}-1,4-dihydro-4-oxo-3-quinolinecarboxylic acid, melting point 210°-5° C., is obtained, which product is then hydrolysed to obtain 1-cyclopropyl-6-fluoro-7-(3-methyl-3-methylamino-1-azetidinyl)-1,4-dihydro-4-oxo-3-quinolinecarboxylic acid, melting point >300° C.

Spectroscopic data: $^1$H NMR, $\delta$,J=Hz, [DMSO-TFAA]; 1.15 (m, 4H); 1.7 (s, 3H); 2.75 (s, 3H); 3.75 (m, 1H); 4.2 (AB, J=7, 4H); 7.0 (d, J=7.6, 1H); 7.85 (d, J=12.9, 1H); 8.6 (s, 1H); 9.4 (broad, 2H). IR(KBr).-2915, 1731, 1629, 1516, cm$^{-1}$.

EXAMPLE 4

Preparation of 1-cyclopropyl-6-fluoro-7-(3-dimethylamino-3-methyl-1-azetidinyl)-1,4-dihydro-4-oxo-3-quinolinecarboxylic acid A mixture of 1.32 g (5 mmol) of 1-cyclopropyl-6,7-difluoro-1,4-dihydro-4-oxo-3-quinolinecarboxylic acid, 1.31 g (7 mmol) of 3-methyl-3-dimethylaminoazetidine hydrochloride and 3 ml of triethylamine in 10 ml of pyridine is heated to reflux for 2 hours. The mixture is evaporated and allowed to cool, ice-cold water is added, the resulting mixture is filtered, the product is washed with water, ethanol and ether and 1.8 g of 1-cyclopropyl-6-fluoro-7-(3-dimethylamiono-3-methyl-1-azetidinyl)-1,4-dihydro-4-oxo-3-quinolinecarboxylic acid, melting point 298°-301° C., are thereby obtained.

Spectroscopic data: $^1$H NMR, $\delta$,J=HZ, [DMSO-TFAA]; 1.16 (m, 4H); 1.67 (s, 3H); 2.78 (s, 6H); 3.67 (m, 1H); 4.29 (AB, J=20, J=9.3, 4H); 7.0 (d, J=7.5, 1H); 7.85 (d, J=12.9, 1H); 8.6 (s, 1H). IR(KBr).-1712, 1629, 1521, 1476 cm$^{-1}$.

EXAMPLE 5

Preparation of 1-cyclopropyl-6,8-difluoro-7-(trans-2-methyl-3-hydroxy-1-azetidinyl)-1,4-dihydro-4-oxo-3-quinolinecarboxylic acid By a procedure completely analogous to that of Example 4, 1-cyclopropyl-6,8-difluoro-7-(trans-2-methyl-3-hydroxy-1-azetidinyl)-1,4-dihydro-4-oxo-3-quinolinecarboxylic acid, melting point 215°–8° C., is obtained.

Spectroscopic data: $^1$H NMR, δ,J=Hz, [DMSO-TFAA]; 8.59 (s, 1H); 7.69 (d, J=13, 1H); 4.55 (m, 2H); 4.01 (m, 3H); 1.45 (d, J=6, 3H); 1.16 (d, J=6, 4H). IR(KBr).-1719, 1628, 1526, 1453, 1412 cm$^{-1}$.

EXAMPLE 6

Preparation of 1-cyclopropyl-6-fluoro-7-(trans-2-methyl-3-hydroxy-1-azetidinyl)-1,4-dihydro-4-oxo-3-quinolinecarboxylic acid By a procedure completely analogous to that described in Example 4, 1-cyclopropyl-6-fluoro-7-(trans-2-methyl-3-hydroxy-1-azetidinyl)-1,4-dihydro-4-oxo-3-quinolinecarboxylic acid, melting point 239°–42° C., is obtained.

Spectroscopic data: $^1$H NMR, δ,J=Hz, [DMSO-TFAA]; 8.58 (s, 1H); 7.79(d, J=13, 1H); 7.01 (d, J=8, 1H); 4.45 (m, 1H); 4.15 (m, 2H); 3.75 (m, 2H); 1.46 (d, J=6, 3H); 1.24 (m, 4H). IR(KBr).-1708, 1630, 1503, 1474, 1460, 1337 cm$^{-1}$.

EXAMPLE 7

Preparation of 1-cyclopropyl-6,8-difluoro-7-[3-methyl-3-(1-pyrrolyl)-1-azetidinyl]-1,4-dihydro-4-oxo-3-quinolinecarboxylic acid By a procedure completely analogous to that described in Example 4, 1-cyclopropyl-6,8-difluoro-7-[3-methyl-3-(1-pyrrolyl)-1-azetidinyl]-1,4-dihydro-4-oxo-3-quinolinecarboxylic acid, melting point 249°–52° C., is obtained.

Spectroscopic data: $^1$H NMR, δ,J=Hz, [Cl$_3$CD]; 1.20 (m, 4H); 1.96 (s, 3H); 3.9 (m, 1H); 4.4–5.0 (complex, 4H); 6.25 (t, J=2, 1H); 6.88 (t, J=2, 1H); 7.77 (dd, J=13, J=2, 1H); 8.66 (s, 1H). IR(KBr).-1727, 1628, 1527, 1446, 1412 cm$^{-1}$.

EXAMPLE 8

Preparation of 1-cyclopropyl-6-fluoro-7-(3-ethylaminomethyl-1-azetidinyl)-1,4-dihydro-4-oxo-3-quinolinecarboxylic acid By a procedure completely analogous to that described in Example 4, 1-cyclopropyl-6-fluoro-7-(3-ethylaminomethyl-1-azetidinyl)-1,4-dihydro-4-oxo-3-quinolinecarboxylic acid, melting point 200°–3° C., is obtained.

Spectroscopic data: $^1$H NMR, δ,J=HZ, [DMSO-TFAA]; 8.52 (s, 1H); 7.69 (d, J=13, 1H); 6.81 (d, J=8, 1H); 4.26 (m, 2H); 3.95 (m, 2H); 3.68 (m, 1H); 2.84 (s, 2H); 2.56 (q, J=7, 2H); 1.26 (m, 4H); 1.04 (t, J=7, 3H). IR(KBr).-1710, 1625, 1477, 1323 cm$^{-1}$.

EXAMPLE 9

Preparation of 1-cyclopropyl-6,8-difluoro-7-(trans-2-methyl-3-amino-1-azetidinyl)-1,4-dihydro-4-oxo-3-quinolinecarboxylic acid By a procedure completely analogous to that described in Example 4, 1-cyclopropyl-6,8-difluoro-7-(trans-2-methyl-3-amino-1-azetidinyl)-1,4-dihydro-4-oxo-3-quinolinecarboxylic acid, melting point 234°–7° C., is obtained.

Spectroscopic data: $^1$H NMR, δ,J=Hz, [DMSO-TFAA]; 8.61 (s, 1H); 8.32 (broad, 2H); 7.70 (dd, J=13, J=1.5, 1H); 4.76 (m, 2H); 4.09 (m, 2H); 3.72 (m, 1H); 1.53 (d, J=6, 3H); 1.16 (d, J=6, 4H). IR(KBr).-1719, 1630, 1578, 1466, 1402, 1319 cm$^{-1}$.

EXAMPLE 10

Preparation of 1-cyclopropyl-6-fluoro-7-(trans-2-methyl-3-amino-1-azetidinyl)-1,4-dihydro-4-oxo-3-quinolinecarboxylic acid By a procedure completely analogous to that described in Example 4, 1-cyclopropyl-6-fluoro-7-(trans-2-methyl-3-amino-1-azetidinyl)-1,4-dihydro-4-oxo-3-quinolinecarboxylic acid, melting point 241°–4° C., is obtained.

Spectroscopic data: $^1$H NMR, δ,J=Hz, [DMSO-TFAA]; 8.61 (s, 1H); 8.37 (broad, 2H); 7.86 (d, J=13, 1H); 7.04 (d, J=8, 1H); 4.53 (m, 2H); 3.92 (m, 3H); 1.54 (d, J=6, 3H); 1.19 (d, J=8, 4H). IR(KBr).-1719, 1629, 1479, 1325 cm$^{-1}$.

EXAMPLE 11

Preparation of 1-cyclopropyl-6-fluoro-7-(3-aminomethyl-1-azetidinyl)-1,4-dihydro-4-oxo-3-quinolinecarboxylic acid By a procedure completely analogous to that described in Example 2, 1-cyclopropyl-6-fluoro-7-(3-trifluoroacetamidomethyl-1-azetidinyl)-1,4-dihydro-4-oxo-3-quinolinecarboxylic acid, melting point 205°–11° C., is obtained, which product is then hydrolysed to obtain 1-cyclopropyl-6-fluoro-7-(3-aminomethyl-1-azetidinyl)-1,4-dihydro-4-oxo-3-quinolinecarboxylic acid, melting point 234°–9° C.

Spectroscopic data: $^1$H NMR, δ,J=Hz, [DMSO-TFAA]; 8.55 (s, 1H); 8.4 (broad, 2H); 7.75 (d, J=13, 1H); 6.85 (d, J=7.6 1H); 4.25 (m, 2H); 4.0 (m, 2H); 3.45 (m, 1H); 3.15 (broad, 3H); 1.11 (m, 4H). IR(KBr).-3368, 1725, 1630, 1479, 1471 cm$^{-1}$.

EXAMPLE 12

Preparation of 1-cyclopropyl-6-fluoro-7-(3-methyl-3-hydroxy-1-azetidinyl)-1,4-dihydro-4-oxo-3-quinolinecarboxylic acid By a procedure completely analagous to that described in Example 4, 1-cyclopropyl-6-fluoro-7-(3-methyl-3-hydroxy-1-azetidinyl)-1,4-dihydro-4-oxo-3-quinolinecarboxylic acid, melting point 303°–8° C., is obtained.

Spectroscopic data: $^1$H NMR, δ,J=Hz, [DMSO-TFAA]; 8.52 (s, 1H); 7.68 (d, J=13, 1H); 6.80 (d, J=7.6 1H); 4.02 (m, 4H); 3.60 (m, 1H); 1.45 (s, 3H); 1.15 (m, 4H). IR(KBr).-1725, 1630, 1514, 1473, 1460 cm$^{-1}$.

EXAMPLE 13

Preparation of 1-cyclopropyl-6-fluoro-7-(3-ethyl-3-hydroxy-1-azetidinyl)-1,4-dihydro-4-oxo-3-quinolinecarboxylic acid By a procedure completely analagous to that described in Example 4, 1-cyclopropyl-6-fluoro-7-(3-ethyl-3-hydroxy-1-azetidinyl)-1,4-dihydro-4-oxo-3-quinolinecarboxylic acid, melting point 284°-7° C., is obtained.

Spectroscopic data: $^1$H NMR, $\delta$, J=Hz, [DMSO-TFAA]; 8.55 (s, 1H); 7.73 (d, J=13, 1H); 6.84 (d, J=7.6, 1H); 4.01 (m, 4H); 3.64 (m, 1H); 1.74 (q, J=7, 2H); 1.17 (m, 4H); 0.9 (t, J=7, 3H). IR(KBr).-1725, 1628, 1513, 1465 cm$^{-1}$.

EXAMPLE 14

Preparation of 1-cyclopropyl-6,8-difluoro-7-(3-ethyl-3-hydroxy-1-azetidinyl)-1,4-dihydro-4-oxo-3-quinolinecarboxylic acid By a procedure completely analagous to that described in Example 4, 1-cyclopropyl-6,8-difluoro-7-(3-ethyl-3-hydroxy-1-azetidinyl)-1,4-dihydro-4-oxo-3-quinolinecarboxylic acid, melting point 257°-9° C., is obtained.

Spectroscopic data: $^1$H NMR, $\delta$, J=Hz, [DMSO-TFAA]; 8.52 (s, 1H); 7.58 (d, J=13, 1H); 4.20 (broad, 4H); 3.90 (m, 1H); 1.71 (q, J=7, 2H); 1.07 (m, 4H); 0.88 (t, J=7, 3H). IR(KBr).-1715, 1626, 1460, 1453, 1412 cm$^{-1}$.

EXAMPLE 15

Preparation of 1-cyclopropyl-6-fluoro-7-(3-amino-3-methyl-1-azetidinyl)-1,4-dihydro-4-oxo-1,8-naphthyridine-3-carboxylic acid A mixture of 0.5 g (1.8 mmol) of 1-cyclopropyl-6-fluoro-7-chloro-1,4-dihydro-4-oxo-1,8-naphthyridine-3-carboxylic acid, 0.34 g (2.1 mmol) of 3-methyl-3-aminoazetidine hydrochloride and 0.5 ml of triethylamine in 10 ml of pyridine is heated to reflux for 3 hours. The mixture is allowed to cool and is filtered and the product is washed with water. 0.52 g of 1-cyclopropyl-6-fluoro-7-(3-amino-3-methyl-1-azetidinyl)-1,4-dihydro-4-oxo-1,8-naphthyridine-3-carboxylic acid, melting point 285°-7° C., is thereby obtained.

Spectroscopic data: $^1$H NMR, $\delta$, J=Hz, [DMSO-TFAA]; 8.59 (s, 1H); 8.4 (broad, 2H); 8.0 (d, J=13, 1H); 4.4 (AB, J=7, 4H); 3.65 (m, 1H); 1.65 (s, 3H); 1.1 (m, 4H). IR(KBr).-2943, 1629, 1447 cm$^{-1}$.

EXAMPLE 16

Preparation of 1-cyclopropyl-6-fluoro-7-(trans-3-amino-2-methyl-1-azetidinyl)-1,4-dihydro-4-oxo-1,8-naphthyridine-3-carboxylic acid By a procedure completely analagous to that described in Example 15, 1-cyclopropyl-6-fluoro-7-(trans-3-amino-2-methyl-1-azetidinyl)-1,4-dihydro-4-oxo-1,8-naphthyridine-3-carboxylic acid, melting point 211°-8° C., is obtained.

Spectroscopic data: $^1$H NMR, $\delta$, J=Hz, [DMSO-TFAA]; 8.6 (s, 1H); 8.4 (broad, 2H); 7.95 (d, J=13, 1H); 4.7 (m, 2H); 4.25 (m, 1H); 3.6 (m, 2H); 1.55 (d, J=6, 3H); 1.1 (m, 4H). IR(KBr).-2943, 1629, 1447 cm$^{-1}$.

EXAMPLE 17

Preparation of (3S)-(−)-10-(3-amino-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 4, (3S)-(−)-10-(3-amino-1-azetidinyl)-9-fluoro-3-methyl-7-oxo-2,3-dihydro-7H-pyrido[1,2,3-de][1,4]benzoxazine-6-carboxylic acid, melting point 236°-40° C., is obtained.

Spectroscopic data: $^1$H NMR, $\delta$, J=Hz, [DMSO-TFAA]; 1.41 (d, J=7, 3H); 3.9–5.1 (complex, 8H); 7.52 (d, J=13, 1H); 8.35 (broad, 2H); 8.88 (s, 1H). IR(KBr).-3350, 1712, 1622, 1536, 1474 cm$^{-1}$. $[\alpha]_D^{20} = -78.8$ (c=4.1, 0.5N NaOH)

EXAMPLE 18

Preparation of (3S)-(−)-10-(3-dimethylamino-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 4, (3S)-(−)-10-(3-dimethylamino-1-azetidinyl)-9-fluoro-3-methyl-7-oxo-2,3-dihydro-7H-pyrido[1,2,3-de][1,4]benzoxazine-6-carboxylic acid, melting point >300° C., is obtained.

Spectroscopic data: $^1$H NMR, $\delta$, J=Hz, [DMSO-TFAA]; 1.41 (d, J=7, 3H); 2.8 (s, 6H); 4.0–5.0 (complex, 8H); 7.52 (d, J=13, 1H); 8.87 (s, 1H). IR(KBr).-2400, 1712, 1619, 1525, 1442, 1340 cm$^{-1}$. $[\alpha]_D^{20} = -79.6$ (c=4.06, 0.5N NaOH)

EXAMPLE 19

Preparation of (3S)-(−)-10-(3-dimethylamino-3-methyl-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 4, (3S)-(−)-10-(3-dimethylamino-3-methyl-1-azetidinyl)-9-fluoro-3-methyl-7-oxo-2,3-dihydro-7H-pyrido[1,2,3-de][1,4]benzoxazine-6-carboxylic acid, melting point 298°-9° C., is obtained.

Spectroscopic data: $^1$H NMR, $\delta$, J=Hz,[DMSO-TFAA]; 1.43 (d, J=6.3, 3H); 1.62 (s, 3H); 2.73 (s, 6H); 4.0–5.0 (complex, 7H); 7.50 (d, J=13, 1H); 8.76 (s, 1H). IR(KBr).-2400, 1712, 1617, 1440, 1420, 1325 cm$^{-1}$. $[\alpha]_D^{20} = -74.6$ (c=4.02, 0.5N NaOH)

EXAMPLE 20

Preparation of (3R)-(+)-10-(3-amino-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 4, (3R)-(+)-10-(3-amino-1-azetidinyl)-9-fluoro-3-methyl-7-oxo-2,3-dihydro-7H-pyrido[1,2,3-de][1,4]benzoxazine-6-carboxylic acid, melting point 236°-40° C., is obtained.

Spectroscopic data: $^1$H NMR, $\delta$, J=Hz,[DMSO-TFAA]; 1.40 (d, J=7, 3H); 3.9–5.1 (complex, 8H); 7.51 (d, J=13, 1H); 8.35 (broad, 2H); 8.87 (s, 1H). IR(KBr).-3350, 1712, 1622, 1536, 1474 cm$^{-1}$. $[\alpha]_D^{20} = +80.1$ (c=4.12, 0.5N NaOH)

EXAMPLE 21

Preparation of (3R)-(+)-10-(3-dimethylamino-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 4, (3R)-(+)-10-(3-dimethylamino-1-azetidinyl)-9-fluoro-3-methyl-7-oxo-2,3-dihydro-7H-pyrido[1,2,3-de][1,4]benzoxazine-6-carboxylic acid, melting point >300° C., is obtained.

Spectroscopic data: $^1$H NMR, δ,J=Hz,[DMSO-TFAA]; 1.40 (d, J=7,3H); 2.8 (s, 6H); 4.0–5.0 (complex, 8H); 7.51 (d, J=13, 1H); 8.88 (s, 1H). IR(KBr).-2400, 1712, 1619, 1525, 1442, 1340 cm$^{-1}$. $[α]_D^{20}$=+82.3 (c=4.16, 0.5N NaOH)

EXAMPLE 22

Preparation of (3R)-(+)-10-(3-dimethylamino-3-methyl-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 4, (3R)-(+)-10-(3-dimethylamino-3-methyl-1-azetidinyl)-9-fluoro-3-methyl-7-oxo-2,3-dihydro-7H-pyrido[1,2,3-de][1,4]benzoxazine-6-carboxylic acid, melting point 298°–9° C., is obtained.

Spectroscopic data: $^1$H NMR, δ,J=Hz,[DMSO-TFAA]; 1.43 (d, J=6.3, 3H); 1.62 (s, 3H); 2.72 (s, 6H); 4.0–5.0 (complex, 7H); 7.51 (d, J=13, 1H); 8.76 (s, 1H). IR(KBr).-2400, 1712, 1617, 1440, 1420, 1325 cm$^{-1}$. $[α]_D^{20}$=+72.8 (c=4.02, 0.5N NaOH)

EXAMPLE 23

Preparation of 1-cyclopropyl-6-fluoro-7-(3-dimethylamino-1-azetidinyl)-1,4-dihydro-4-oxo-1,8-naphthyridine-3-carboxylic acid By a procedure completely analogous to that described in Example 15, 1-cyclopropyl-6-fluoro-7-(3-dimethylamino-1-azetidinyl)-1,4-dihydro-4-oxo-1,8-naphthyridine-3-carboxylic acid, melting point 249°–51° C., is obtained.

Spectroscopic data: $^1$H NMR, δ,J=Hz,[DMSO-TFAA]; 1.13 (m, 4H); 2.86 (s, 6H); 3.66 (m, 1H); 4.35 (m, 1H); 4.45 (m, 4H); 8.04 (d, J=11.4, 1H); 8.59 (s, 1H). IR(KBr).-1716, 1634, 1511, 1452 cm$^{-1}$.

EXAMPLE 24

Preparation of 1-cyclopropyl-6-fluoro-7-(3-methylamino-1-azetidinyl)-1,4-dihydro-4-oxo-1,8-naphthyridine-3-carboxylic acid By a procedure completely analogous to that described in Example 2, 1-cyclopropyl-6-fluoro-7-{3-[N-(methyl)trifluoromethylacetamido]-1-azetidinyl}-1,4-dihydro-4-oxo-1,8-naphthyridine-3-carboxylic acid, melting point 206°–12° C., is obtained, which product is then hydrolysed to obtain 1-cyclopropyl-6-fluoro-7-(3-methylamino-1-azetidinyl)-1,4-dihydro-4-oxo-1,8-naphthyridine-3-carboxylic acid, melting point 250°–3° C.

Spectroscopic data: $^1$H NMR, δ,J=Hz,[DMSO-TFAA]; 1.11 (m, 4H); 2.64 (s, 3H); 3.65 (m, 1H); 4.15 (m, 1H); 4.44 (m, 4H); 7.97 (d, J=11.4, 1H); 8.56 (s, 1H); 9.24 (broad, 1H). IR(KBr).-2932, 1631, 1614, 1457, 1276 cm$^{-1}$.

EXAMPLE 25

Preparation of 1-cyclopropyl-6,8-difluoro-7-[(3R)-trans-2,3-dimethyl-3-hydroxy-1-azetidinyl]-1,4-dihydro-4-oxo-3-quinolinecarboxylic acid By a procedure completely analogous to that described in Example 4, 1-cyclopropyl-6,8-difluoro-7-(trans-2,3-dimethyl-3-hydroxy-1-azetidinyl)-1,4-dihydro-4-oxo-3-quinolinecarboxylic acid, melting point 246°–51° C., is obtained.

Spectroscopic data: $^1$H NMR, δ,J=Hz,[DMSO-TFAA]; 8.59 (s, 1H); 7.68 (dd, J=13, J=1.5, 1H); 4.54 (m, 1H); 4.27 (m, 1H); 4.02 (m, 2H); 1.35 (m, 6H); 1.16 (d, J=6, 4H). IR(KBr).-3470, 1705, 1626, 1529, 1475, 1458, 1414 cm$^{-1}$.

EXAMPLE 26

Preparation 1-cyclopropyl-6-fluoro-7-[(3R)-trans-2,3-dimethyl-3-hydroxy-1-azetidinyl]-1,4-dihydro-4-oxo-3-quinolinecarboxylic acid By a procedure completely analogous to that described in Example 4, 1-cyclopropyl-6-fluoro-7-(trans-2,3-dimethyl-3-hydroxy-1-azetidinyl)-1,4-dihydro-4-oxo-3-quinolinecarboxylic acid, melting point 284°–90° C., is obtained.

Spectroscopic data: $^1$H NMR, δ,J=Hz,[DMSO-TFAA]; 8.57 (s, 1H); 7.77 (d, J=13, 1H); 7.05 (d, J=7, 1H); 4.16 (m, 2H); 3.81 (m, 2H); 1.32 (m, 10H). IR(KBr).-3450, 1706, 1630, 1503, 1475 cm$^{-1}$.

EXAMPLE 27

Preparation of 5-amino-1-cyclopropyl-6,8-difluoro-7-(3-hydroxy-1-azetidinyl)-1,4-dihydro-4-oxo-3-quinolinecarboxylic acid By a procedure completely analogous to that of Example 4, 5-amino-1-cyclopropyl-6,8-difluoro-7-(3-hydroxy-1-azetidinyl)-1,4-dihydro-4-oxo-3-quinolinecarboxylic acid, melting point 271°–5° C., is obtained.

Spectroscopic data: $^1$H NMR, δ,J=Hz,[DMSO-TFAA]; 8.43 (s, 1H); 6.98 (s, 2H); 4.58 (m, 3H); 4.05 (m, 3H); 1.07 (m, 4H). IR(KBr).-3340, 1690, 1540, 1423 cm$^{-1}$.

EXAMPLE 28

Preparation of 1-cyclopropyl-6,8-difluoro-7-(trans-3-dimethylamino-2-methyl-1-azetidinyl)-1,4-dihydro-4-oxo-3-quinolinecarboxylic acid By a procedure completely analogous to that described in Example 4, 1-cyclopropyl-6,8-difluoro-7-(trans-3-dimethylamino-2-methyl-1-azetidinyl)-1,4-dihydro-4-oxo-3-quinolinecarboxylic acid, melting point 149°–151° C., is obtained.

Spectroscopic data: $^1$H NMR, δ,J=HZ[DMSO-TFA]; 8.61 (s, 1H); 7.75 dd, J=13, J=1.5, 1H); 4.98 (m, 1H); 4.67 (m, 1H); 4.34 (m, 1H); 3.92 (m, 2H); 2.83 (s, 6H); 154 (d, J=6, 3H); 1.16 (d, J=6, 4H). IR(KBr).-1729, 1627, 1523, 1459, 1328 cm$^{-1}$.

EXAMPLE 29

Preparation of
1-cyclopropyl-6-fluoro-7-(trans-3-dimethylamino-2-methyl-1-azetidinyl)-1,4-dihydro-4-oxo-3-quinolinecarboxylic acid By a procedure completely analogous to that of Example 4, 1-cyclopropyl-6-fluoro-7-(trans-3-dimethylamino-2-methyl-1-azetidinyl)-1,4-dihydro-4-oxo-3-quinolinecarboxylic acid, melting point 181°–5° C., is obtained.

Spectroscopic data: $^1$H NMR, $\delta$,J=HZ[DMSO-TFA]; 8.64 (s, 1H); 7.9 (d, 1H, J=12 Hz); 7.12 (d, 1H, J=7 Hz); 4.67 (m, 2H); 4.23 (m, 1H); 3.83 (m, 2H); 2.85 (s, 6H); 1.57 (d, 3H, J=5 Hz); 1.18 (m, 4H). IR(KBr).-2890, 1727, 1630, 1510, 1468 cm$^{-1}$.

EXAMPLE 30

Preparation of
(3S)-(−)-10-(3-ethylaminomethyl-3-methyl-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 2, (3S)-(−)-10-{3-methyl-3-[N-(ethyl)trifluoromethylacetamidomethyl]-1-azetidinyl}-9-fluoro-3-methyl-7-oxo-2,3-dihydro-7H-pyrido[1,2,3-de][1,4]benzoxazine-6-carboxylic acid, melting point 234°–238° C., is obtained.

Spectroscopic data: $^1$H NMR, $\delta$,J=Hz,[DMSO-TFA]; 1.19 (t, J=7 Hz, 3H); 1.31 (s, 3H); 1.45 (d, J=7 Hz, 3H); 3.44 (m, 2H); 3.66 (s, 2H); 3.90–4.60 (m, 6H); 4.75 (m, 1H); 7.45 (d, J=14 Hz, 1H); 8.76 (s, 1H). IR(KBr).-1718, 1690, 1622, 1466, 1449, 1137 cm$^{-1}$.

The above product is hydrolysed with 10% sodium hydroxide to obtain (3S)-(−)-10-(3-ethylaminomethyl-3-methyl-1-azetidinyl)-9-fluoro-3-methyl-7-oxo-2,3-dihydro-7-pyrido[1,2,3-de][1,4]benzoxazine-6-carboxylic acid, melting point 242°–5° C.

Spectroscopic data: $^1$H NMR, $\delta$,J=Hz,[DMSO-TFA]; 1.22 (t, J=7 Hz, 3H); 1.38 (s, 3H); 1.42 (d,J=8 Hz, 3H); 2.8–3.4 (m, 4H); 3.9–4.6 (m, 6H); 4.84 (m, 1H); 7.48 (d, J=14 Hz, 1H); 8.34 (b, 1H); 8.86 (s, 1H). IR(KBr).-2980, 1686, 1621, 1534, 1474, 1459 cm$^{-1}$. $[\alpha]_D^{23}$=−56.1 (c=4.8, 0.5N NaOH)

EXAMPLE 31

Preparation of
(3R)-(−)-10-(3-ethylaminomethyl-3-methyl-1-azetidinyl)-9-fluoro-3-methyl-7-oxo-2,3-dihydro-7H-pyrido[1,2,3-de][1,4]benzoxazine-6-carboxylic acid By a procedure completely analogous to that described in Example 2, (3R)-(−)-10-{3-methyl-3-[N-(ethyl)trifluoromethylacetamidomethyl]-1-azetidinyl}-9-fluoro-3-methyl-7-oxo-2,3-dihydro-7H-pyrido[1,2,3-de][1,4]benzoxazine-6-carboxylic acid, melting point 233°–236° C., is obtained.

Spectroscopic data: $^1$H NMR, $\delta$,J=Hz,[DMSO-TFA]; 1.19 (t, J=7 Hz, 3H), 1.31 (s, 3H); 1.45 (d, J=7 Hz, 3H); 3.44 (m, 2H); 3.66 (s, 2H); 3.90–4.60 (m, 6H); 4.75 (m, 1H); 7.45 (d, J=14 Hz, 1H); 8.76 (s, 1H). IR(KBr).-1718, 1690, 1622, 1466, 1449, 1137 cm$^{-1}$.

The above product is hydrolysed with 10% sodium hydroxide to obtain (3R)-(−)-10-(3-ethylaminomethyl-3-methyl-1-azetidinyl)-9-fluoro-3-methyl-7-oxo-2,3-dihydro-7H-pyrido[1,2,3-de][1,4]benzoxazine-6-carboxylic acid, melting point 242°–5° C.

Spectroscopic data: $^1$H NMR, $\delta$,J=Hz, [DMSO-TFA]; 1.22 (t, J=7 Hz, 3H); 1.38 (s, 3H); 1.42 (d, J=8 Hz, 3H); 2.8–3.4 (m, 4H); 3.9–4.6 (m, 6H); 4.84 (m, 1H); 7.48 (d, J=14 Hz, 1H); 8.34 (b 1H); 8.86 (s, 1H); IR(KBr).-2980, 1686, 1621, 1534, 1474, 1459 cm$^{-1}$. $[\alpha]_D^{23}$=+55.4 (c=4.5, 0.5N NaOH).

EXAMPLE 32

Preparation of
1-cyclopropyl-6-fluoro-7-(trans-3-aminomethyl-2-methyl-1-azetidinyl)-1,4-dihydro-4-oxo-3-quinolinecarboxylic acid, melting point 222°–7° C.

Spectroscopic data: $^1$H NMR, $\delta$,J=Hz,[DMSO-TFA]; 8.58 (s, 1H); 8.25 (b, 2H); 7.81 (d, 1H, J=13.7); 6.95 (d, 1H, J=7.6 Hz); 4.35 (m, 1H); 3.78 (m, 1H); 3.17 (m, 2H); 253 (m, 3H); 1.50 (d, 3H, J=5.7); 1.21 (m, 4H). IR(KBr).-3420, 1675, 1629, 1509, 1476 cm$^{-1}$.

EXAMPLE 33

Preparation of
1-cyclopropyl-6,8-difluoro-7-(trans-3-aminomethyl-2-methyl-1-azetidinyl)-1,4-dihydro-4-oxo-3-quinolinecarboxylic acid By a procedure completely analogous to that described in Example 4, 1-cyclopropyl-6,8-difluoro-7-(trans-3-aminomethyl-2-methyl-1-azetidinyl)-1,4-dihydro-4-oxo-3-quinolinecarboxylic acid, melting point 196°–203° C., is obtained.

Spectroscopic data: $^1$H NMR, $\delta$,J=Hz[DMSO-TFA]; 8.58 (s, 1H); 7.86 (broad, 2H); 7.69 (d, 1H, J=13 Hz); 4.58 (m, 1H); 4.04 (m, 1H); 3.20 (m, 2H); 2.53 (m, 3H); 1.49 (d, 3H, J=5.0 Hz); 1.18 (m, 4H), IR(KBr).-3400, 1608, 1578, 1475, 1295 cm$^{-1}$.

EXAMPLE 34

Preparation of
1-cyclopropyl-6-fluoro-7-(trans-3-methylamino-2-methyl-1-azetidinyl)-1,4-dihydro-4-oxo-3-quinolinecarboxylic acid By a procedure completely analogous to that described in Example 2, 1-cyclopropyl-6-fluoro-7-(trans-3-methylamino-2-methyl-1-azetidinyl)-1,4-dihydro-4-oxo-3-quinolinecarboxylic acid, melting point 208°–12° C., is obtained.

Spectroscopic data: $^1$H NMR, $\delta$, J=Hz[DMSO-TFA]; 9.4 (b, 2H); 8.65 (s, 1H); 7.85 (d,1H; J=12Hz); 7.1 (d, 1H, J=7.6 Hz); 4.65 (m, 2H); 4.2 (m, 1H); 3.85 (m, 2H); 2.7 (s, 3H); 1.5 (d, 3H, J=5 Hz); 1.2 (m, 4H). IR(KBr).-2930, 1626, 1500, 1323, 1286 cm$^{-1}$.

EXAMPLE 35

Preparation of
1-cyclopropyl-6,8-difluoro-7-(trans-3-methylamino-2-methyl-1-azetidinyl)-1,4-dihydro-4-oxo-3-quinolinecarboxylic acid By a procedure completely analogous to that described in Example 2, 1-cyclopropyl-6,8-difluoro-7-(trans-3-methylamino-2-methyl-1-azetidinyl)-1,4-dihydro-4-oxo-3-quinolinecarboxylic acid, melting point 241°–6° C., is obtained.

Spectroscopic data: $^1$H NMR, $\delta$, J=Hz[DMSO-TFA]; 9.23 (b, 2H); 8.65 (s, 1H); 7.77 (d, 1H, J=13Hz); 4.87 (m, 2H); 3.77 (m, 1H); 2.66 (s, 3H); 1.58 (d, 3H); 1.58 (d, 3H, J=5 Hz); 1.19 (d, 4H, J=5.6 Hz). IR(KBR).-2930, 1625, 1461, 1322 cm$^{-1}$.

EXAMPLE 36

Preparation of
1-cyclopropyl-6-fluoro-7-(trans-3-ethylaminomethyl-2-methyl-1-azetidinyl)-1,4-dihydro-4-oxo-3-quinolinecarboxylic acid By a procedure completely analogous to that described in Example 4, 1-cyclopropyl-6-fluoro-7-(trans-3-ethylaminomethyl-2-methyl-1-azetidinyl)-1,4-dihydro-4-oxo-3-quinolinecarboxylic acid, melting point 219°–25° C., is obtained.

Spectroscopic data: $^1$H NMR, δ,J=Hz[DMSO-TFA]; 8.49 (s, 1H, J=14 Hz); 6.94 (d, 1H, J=6.8 Hz); 4.35 (m, 2H); 3.55–4.1 (m, 3H); 3.25 (m, 2H); 2.95 (d, 2H, J=4.8); 1.48 (d, 3H, J=5 Hz); 1.2 (m, 7H). IR(KBr).-1686, 1631, 1520, 1470, 1202 cm$^{-1}$.

EXAMPLE 37

Preparation of
1-cyclopropyl-6,8-difluoro-7-(trans-3-ethylaminomethyl-2-methyl-1-azetidinyl)-1,4-dihydro-4-oxo-3-quinolinecarboxylic acid By a procedure completely analogous to that described in Example 4, 1-cyclopropyl-6,8-difluoro-7-(trans-3-ethylaminomethyl-2-methyl-1-azetidinyl)-1,4-dihydro-4-oxo-3-quinolinecarboxylic acid, melting point 209°–12° C., is obtained.

Spectroscopic data: $^1$H NMR, δ,J=Hz[DMSO-TFA]; 8.55 (s, 1H); 7.65 (d, 1H, J=13 Hz); 4.49 (m, 2H); 3.95 (m, 3H); 3.43 (m, 2H); 2.72 (d, 2H, J=4.8 Hz); 1.47 (d, 3H, J=5.3 Hz); 1.08 (m, 7H). IR(KBr).-1624, 1577, 1468, 1323, 1290 cm$^{-1}$.

EXAMPLE 38

Preparation of
1-cyclopropyl-6,8-difluoro-7-(trans-3-hydroxy-2-ethyl-1-azetidinyl)-1,4-dihydro-4-oxo-3-quinolinecarboxylic acid By a procedure completely analogous to that of Example 4, 1-cyclopropyl-6,8-difluoro-7-(trans-3hydroxy-3-ethyl-1-azetidinyl)-1,4-dihydro-4-oxo-3-quinolinecarboxylic acid, melting point 259°–61° C., is obtained.

Spectroscopic data: $^1$H NMR, δ, J=Hz[DMSO-TFA]; 0.7–1.4 (m, 7H); 1.5–2.2 (m, 2H); 3.8–4.4 (m, 5H); 7.65 (d, J=13.0 Hz, 1H); 8.58 (s, 1H). IR(KBr).-3406, 1714, 1706, 1628, 1526, 1411 cm$^{-1}$.

EXAMPLE 39

Preparation of
1-cyclopropyl-6-fluoro-7-(trans-3-hydroxy-2-ethyl-1-azetidinyl)-1,4-dihydro-4-oxo-3-quinolinecarboxylic acid By a procedure completely analogous to that of Example 4, 1-cyclopropyl-6-fluoro-7-(trans-3-hydroxy-2-ethyl-1-azetidinyl)-1,4-dihydro-4-oxo-3-quinolinecarboxylic acid, melting point 250°–5° C., is obtained.

Spectroscopic data: $^1$H MNR, δ, J=Hz[DMSO-TFA]; 0.97 (t, J=7.3 Hz, 3H); 1.20 (m, 4H); 1.60–2.00 (m, 2H); 3.72 (m, 1H); 4.05 (m, 1H); 4.32 (m, 2H); 4.69 (m, 1H); 6.92 (d, J=8.0 Hz, 1H); 7.74 (d, J=13.0 Hz, 1H); 8.55 (s, 1H). IR(KBr).-3387, 1706, 1631, 1513, 1473, 1390 cm$^{-1}$.

EXAMPLE 40

Preparation of
1-cyclopropyl-6,8-difluoro-7-{trans-3-[N-(methyl)trifluoroacetamido]-2-methyl-1-azetidinyl}-1,4-dihydro-4-oxo-3-quinolinecarboxylic acid A mixture of 2.6 g (9.2 mmol) of 1-cyclopropyl-6,7,8-trifluoro-1,4-dihydro-4-oxo-3-quinolinecarboxylic acid, 2.57 g (11 mmol) of 3-[N-(methyl)trifluoroacetamido]-2-methylazetidine hydrochloride and 3 g (30 mmol) of triethylamine in 30 ml of pyridine is heated to reflux for 2 hours. The mixture is evaporated under vacuum, the residue is diluted with ice-cold water, the resulting mixture is filtered and the product is washed with water. 2.5 g are obtained. The product is recrystallized from acetonitrile. 2.25 g of 1-cyclopropyl-6,8-difluoro-7-{trans-3-[N-(methyl)trifluoroacetamido]-2-methyl-1-azetidinyl}-1,4-dihydro-4-oxo-3-quinolinecarboxylic acid, melting point 246°–9° C., are obtained. $^1$H NMR, δ,J=Hz[DMSO]; 14.1, (s, 1H); 8.6 (s, 1H); 7.75 (d, 1H, J=13 Hz); 4.5 (m, 5H); 3.2 (s, 3H). IR(KBr).-1730, 1704, 1627, 1466 cm$^{-1}$.

EXAMPLE 41

Preparation of
1-cyclopropyl-6,8-difluoro-7-[3-(1-pyrrolidinyl)-1-azetidinyl]-1,4-dihydro-4-oxo-3-quinolinecarboxylic acid By a procedure completely analogous to that of Example 4, 1-cyclopropyl-6,8-difluoro-7-[3-(1-pyrrolidinyl)-1-azetidinyl]-1,4-dihydro-4-oxo-3-quinolinecarboxylic acid, melting point 224°–7° C., is obtained.

Spectroscopic data: $^1$H NMR, δ,J=Hz[DMSO-TFAA]; 10.83 (b, 1H); 7.78 (d, J=13, 1H); 4.62 (m, 4H); 4.35 (m, 1H); 4.06 (m, 1H); 3.67 (m, 2H); 3.15 (m, 2H); 2.01 (m, 4H); 1.21 (m, 4H). IR(KBr).-1721, 1627, 1550, 1529, 1474, 1451 cm$^{-1}$.

EXAMPLE 42

Preparation of
1-cyclopropyl-6,8-difluoro-7-(cis-3-amino-2-methyl-1azetidinyl)-1,4-dihydro-4-oxo-3-quinolinecarboxylic acid By a procedure completely analogous to that described in Example 4, 1-cyclopropyl-6,8-difluoro-7-(cis-3-amino-2-methyl-1-azetidinyl)-1,4-dihydro-4-oxo-3-quinolinecarboxylic acid, melting point 215°–8° C., is obtained.

Spectroscopic data: $^1$H NMR, δ,J=Hz[DMSO-TFA]; 8.57 (s, 1H); 8.39 (b, 2H); 7.69 (d, J=13, 1H); 5.01 (m, 1H); 4.39 (m, 3H); 3.99 (m, 1H); 1.48 (d, J=6, 3H); 1.12 (d, J=6, 4H). IR(KBr).-3385, 1725, 1626, 1523, 1412, 1337, 803 cm$^{-1}$.

EXAMPLE 43

Preparation of
1-cyclopropyl-6-fluoro-7-(cis-3-amino-2-methyl-1-azetidinyl)-1,4-dihydro-4-oxo-3-quinolinecarboxylic acid By a procedure completely analogous to that described in Example 4, 1-cyclopropyl-6-fluoro-7-(cis-3-amino-2-methyl-1-azetidinyl)-1,4-dihydro-4-oxo-3-quinolinecarboxylic acid, melting point 222°–5° C., is obtained.

Spectroscopic data: $^1$H NMR, δ,J=Hz[DMSO-TFA]; 8.52 (s, 1H); 8.46 (b, 2H); 7.75 (d, J=13, 1H); 6.98 (d, J=8, 1H); 4.77 (m, 1H); 4.25 (m, 3H); 3.64 (m, 1H); 1.49 (d, J=6, 3H); 1.18 (d, J=8, 4H). IR(KBr).-3387, 1725, 1631, 1490, 1464, 1341 cm$^{-1}$.

EXAMPLE 44

Preparation of 1-cyclopropyl-6,8-difluoro-7-(r-3amino-3-trans-2-dimethyl-1-azetidinyl)-1,4-dihydro-4-oxo-3-quinolinecarboxylic acid By a procedure completely analogous to that described in Example 4, 1-cyclopropyl-6,8-difluoro-7-(r-3-amino-3-trans-2-dimethyl-1-azetidinyl)-1,4-dihydro-4-oxo-3-quinolinecarboxylic acid, melting point 265°–268° C., is obtained.

Spectroscopic data: $^1$H NMR, δ,J=Hz[DMSO-TFA]; 8.63 (s, 1H); 7.77 (d, J=13, 1H); 4.83 (m, 1H); 4.33 (m, 2H); 4.05 (m, 1H); 1.49 (s, 3H); 1.44 (d, J=6, 3H); 1.17 (d, J6, 4H). IR(KBr).-3380, 1719, 1628, 1460 cm$^{-1}$.

EXAMPLE 45

Preparation of 1-cyclopropyl-6-fluoro-7-(r-3-amino-3-trans-2-dimethyl-1-azetidinyl)-1,4-dihydro-4-oxo-3-quinolinecarboxylic acid By a procedure completely analogous to that described in Example 4, 1-cyclopropyl-6-fluoro-7-(r-3-amino-3-trans-2-dimethyl-1-azetidinyl)-1,4-dihydro-4-oxo-3-quinolinecarboxylic acid, melting point 269°–272° C., is obtained.

Spectroscopic data: $^1$H NMR, δ,J=Hz[DMSO-TFA]; 8.61 (s, 1H); 8.42 (b, 2H); 7.86 (d, J=13, 1H); 7.09 (d, J=8, 1H); 4.54 (m, 1H); 4.15 (m, 2H); 3.77 (m, 1H); 1.50 (s, 3H); 1.43 (d, J=6, 3H); 1.18 (d, J=6, 4H). IR(KBr).-3375,1629,1500,1478.1326 cm$^{-1}$.

EXAMPLE 46

Preparation of 1-cyclopropyl-6,9-difluoro-7-(cis-3-hydroxy-2-methyl-1-azetidinyl) -1,4-dihydro-2 4-oxo-3-quinolinecarboxylic acid By a procedure completely analogous to that described in Example 4, 1-cyclopropyl-6,8-difluoro-7-(cis-3-hydroxy-2-methyl-1-azetidinyl) -1,4-dihydro-4-oxo-3quinolinecarboxylic acid, melting point 235°–8° C., is obtained.

Spectroscopic data: $^1$H NMR, δ,J=Hz [DMSO-TFA]; 8.57 (s, 1H); 8.39 (b, 2H); 7.69 (d, J=13, 1H); 5.01 (m, 1H); 4.39 (m, 2H); 3.99 (m, 1H); 1.47 (d, J=7, 3H); 1.11 (d, J=6, 4H). IR)KBr).-3371, 1708, 1624, 1525, 1476, 1325, 803 cm$^{-1}$.

EXAMPLE 47

Preparation of 1-cyclopropyl-6-fluoro-7-(cis-3-hydroxy-2-methyl-1-azetidinyl)-1,4-dihydro-4-oxo-3-quinolinecarboxylic acid By a procedure completely analogous to that described in Example 4, 1-cycolopropyl-6-fluoro-7-(cis-3-hydroxy-2-methyl-1-azetidinyl)-1,4-dihydro-4oxo-3-quinolinecarboxylic acid, melting point 236°–240° C., is obtained.

Spectroscopic data: $^1$H NMR, δ,J=Hz[DMDO-TFA]; 8.52 (s, 1H); 8.45 (b, 2H); 7.74 (d, J=13, 1H); 6.98 (d, J=8, 1H); 4.77 (m, 1H); 4.25 (m, 2H); 3.64 (m, 1H); 1.49 (d, J=6, 3H); 1.15 (d, J=6, 4H). IR(KBr).-3446, 1708, 1632, 1514, 1473, 1339 cm$^{-1}$.

EXAMPLE 48

Preparation of ethyl 1-cyclopropyl-6,8-difluoro-7-(3-amino-3-methyl-1-azetidinyl)-1,4-dihydro-4-oxo-3-quinolinecarboxylate.

By a procedure completely analogous to that of Example 4, the ethyl ester of 1-cyclopropyl-6,8-difluoro-7-(3-amino-3-methyl-1-azetidinyl)-1,4-dihydro-4-oxo-3-quinolinecarboxylic acid, melting point 175°–81° C., is obtained.

Spectroscopic data: $^1$H NMR, δ, [CDCl$_3$]; 8.46 (s, 1H); 7.78 (dd, 1H, J=13 Hz); 4.36 (q, 2H, J=7 Hz); 4.3 (d, 2H, J=8 Hz); 3.92 (m, 1H); 1.80 (b, 2H); 1.53 (s, 3H); 1.39 (+, 3H, J=7 Hz); 1.15 (m, 4H). IR(KBr).-1727, 1619, 1480, 1318, 800 cm$^{-1}$.

EXAMPLE 49

Preparation of 5-amino-1-cyclopropyl-6,8-difluoro -7-(trans-3amino-2-methyl-1-azetidinyl)-1,4-dihydro-4-oxo-3-quinolinecarboxylic acid By a procedure completely analogous to that of Example 4, 5-amino-1-cyclopropyl-6,8-difluoro-7-(trans-3-amino-2methyl-1-azetidinyl)-1,4-dihydro-4-oxo-3-quinolinecarboxylic acid, melting point 206°–210° C., is obtained.

Spectroscopic data: $^1$H NMR, δ, [DMSO-TFA]; 1.05 (m, 1H); 1.40 (d, J=5 Hz, 3H); 3.46 (m, 1H); 3.78 (m, 1H); 4.0 (m, 1H); 4.59 (m, 2H); 8.25 (b, 2H); 8.33 (s, 1H). IR(KBr).-3419, 1710, 1632, 1518, 1432, 1304 cm$^{-1}$.

EXAMPLE 50

Preparation of 1-cyclopropyl-6,8-difluoro-7-(3-ethylamino-1-azetidinyl)-1,4-dihydro-4-oxo-3-qinolinecarboxylic acid By a procedure completely analogous to that of Example 4, 1-cyclopropyl-6,8-difluoro-7-(3-ethylamino-1-azetidinyl)-1,4-dihydro-4-oxo-3-quinolinecarboxylic acid, melting point 222°–7° C., is obtained.

Spectroscopic data: $^1$H NMR, δ,J=Hz; [DMSO-d$_6$-TFAA]; 9.29 (b, 2H); 8.58 (1, 1H); 7.71 (d, J=13); 4.61 (m, 4H); 4.06 (m, 2H); 3.43 (m, 2H); 1.19 (m, 7H). IR(KBr).-1620, 1585, 1472, 1403, 1328 cm$^{-1}$.

EXAMPLE 51

Preparation of 1-cyclopropyl-6-fluoro-7-(3-ethylamino-1-azetidinyl-1,4-dihydro-4-oxo-3-quinolinecarboxylic acid By a procedure completely analogous to that of Example 2, 1-cyclopropyl-6-fluoro-7-(3-ethylamino-1-azetidinyl)-1,4-dihydro-4-oxo-3-quinolinecarboxylic acid, melting point 220°–4° C., is obtained.

Spectroscopic data: $^1$H NMR, δ,J=Hz; [DMSO-d$_6$-TFAA]; 9.30 (b, 2H); 8.60 (1, 1H); 7.85 (d, J=13, 1H); 6.99 (d, J=7.6, 1H); 4.34 (m, 5); 3.75 (m, 1H); 3.02 (m, 2H); 1.23 (m, 7H). IR(KBr).-1689, 1630, 1516, 1475, 1185 cm$^{-1}$.

EXAMPLE 52

Preparation of
1-cyclopropyl-6,8-difluoro-7-(cis-3-amino-2-ethyl-1-azetidinyl)-1,4-dihydro-4-oxo-3-quinolinecarboxylic acid By a procedure completely analogous to that of Example 4, 1-cyclopropyl-6,8-difluoro-7-(cis-3-amino-2-ethyl-1-azetidinyl)-1,4-dihydro-4-oxo-3-quinolinecarboxylic acid, melting point 230°–234° C. (dec.), is obtained.

Spectroscopic data: $^1$H NMR, δ,J=Hz[DMSO-TFA]: 0.94 (t, J=6.5 Hz, 3H); 1.17 (m, 4H); 1.92 (m, 2H); 4.09 (m, 1H); 4.35 (m, 3H); 4.82 (m, 1H); 7.74 (d, J=13.3 Hz, 1H); 8.49 (m, 2H); 8.60 (s, 1H). IR(KBr).-3393, 3318, 1726, 1628, 1544, 1498, 1491, 806 cm$^{-1}$.

EXAMPLE 53

Preparation of
1-cyclopropyl-6-fluoro-7-(cis-3-amino-2-ethyl-1-azetidinyl)-1,4-dihydro-4-oxo-3-quinolinecarboxylic acid By a procedure completely analogous to that of Example 4, 1-cyclopropyl-6-fluoro-7-(cis-3-amino-2-ethyl-1-azetidinyl)-1,4-dihydro-4-oxo-3-quinolinecarboxylic acid, melting point 236°–237° C., is obtained.

Spectroscopic data: $^1$H NMR, δ,J=Hz[DMSO-TFA]: 0.90–1.50 (m, 7H); 1.98 (m, 2H); 3.77 (m, 1H); 4.30 (m, 3H); 4.59 (m, 1H); 7.13 (d, J=8.0 Hz, 1H); 7.81 (d, J=13.0 Hz, 1H); 8.57 (s, 1H); 9.03 (b, 2H); IR(KBr).-3388, 3318, 1725, 1631, 1509, 1774, 818 cm$^{-1}$.

EXAMPLE 54

Preparation of
1-ethyl-6,8-difluoro-7-(trans-3-amino-2-methyl-1-azetidinyl)-1,4-dihydro-4-oxo-3-quinolinecarboxylic acid By a procedure completely analogous to that described in Example 4, 1-ethyl-6,8-difluoro-7-(trans-3-amino-2-methyl-1-azetidinyl)-1,4-dihydro-4-oxo-3-quinolinecarboxylic acid, melting point 215°–217° C., is obtained.

Spectroscopic data: $^1$H NMR, δ,J=Hz,[DMSO-TFA]: 1.5 (m, 6H); 3.7 (m, 1H); 4.2 (m, 1H); 4.65 (m, 4H); 7.8 (d, J=13 Hz, 1H); 8.5 (b, 2H); 8.86 (s, 1H). IR(KBr).-3105, 1625, 1467 cm$^{-1}$.

EXAMPLE 55

Preparation of
1-ethyl-6-fluoro-7-(trans-3-amino-2-methyl-1-azetidinyl)-1,4-dihydro-4-oxo-3-quinolinecarboxylic acid By a procedure completely analogous to that described in Example 4, 1-ethyl-6-fluoro-7-(trans-3-amino-2-methyl-1-azetidinyl)-1,4-dihydro-4-oxo-3-quinolinecarboxylic acid, melting point 232°–235° C., is obtained.

Spectroscopic data: $^1$H NMR, δ,J=Hz,[DMSO]: 1.38 (m, 6H); 3.5 (m, 4H); 4.0 (m, 1H); 4.5 (m, 3H); 6.56 (d, J=7 Hz, 1H); 7.8 (d, J=13 Hz, 1H); 8.83 (s, 1H). IR(KBr).-3310, 1723, 1630, 1450 cm$^{-1}$.

EXAMPLE 56

Preparation of
1-(2,4-difluorophenyl)-6,8-difluoro-7-(trans-3-amino-2-methyl-1-azetidinyl)-1,4-dihydro-4-oxo-3-quinolinecarboxylic acid By a procedure completely analogous to that described in Example 4, 1-(2,4-difluorophenyl)-6,8-difluoro-7-(trans-3-amino-2-methyl-1-azetidinyl)-1,4-dihydro-4-oxo-3-quinolinecarboxylic acid, melting point 200°–204° C., is obtained.

Spectroscopic data: $^1$H NMR, δ,J=Hz,[DMSO-TFA]: 1.4 (d, J=6 Hz, 3H); 3.65 (m, 1H); 4.1 (m, 1H); 4.6 (m, 2H); 7.81 (m, 4H); 8.34 (b, 2H); 8.61 (s, 1H). IR(KBr).-1619, 1509, 1474 cm$^{-1}$.

EXAMPLE 57

Preparation of
1-(2,4-difluorophenyl)-6-fluoro-7-(trans-3-amino-2-methyl-1-azetidinyl)-1,4-dihydro-4-oxo-3-quinolinecarboxylic acid By a procedure completely analogous to that described in Example 4, 1-(2,4-difluorophenyl)-6-fluoro-7-(trans-3-amino-2-methyl-1-azetidinyl)-1,4-dihydro-4-oxo-3-quinolinecarboxylic acid, melting point 203°–205° C., is obtained.

Spectroscopic data: $^1$H NMR, δ,J=Hz, [DMSO-TFA]: 1.32 (d, J=6 Hz, 3H); 3.78 (m, 2H); 4.3 (m, 2H); 5.78 (d, J=7 Hz, 1H); 8.0 (m, 4H); 8.3 (b, 2H); 8.7 (s, 1H). IR(KBr).-2950, 1628, 1509 cm$^{-1}$.

EXAMPLE 58

Preparation of
1-(4-fluorophenyl)-6-fluoro-7-(trans-3-amino-2-methyl-1-azetidinyl)-1,4-dihydro-4-oxo-3-quinolinecarboxylic acid By a procedure completely analogous to that described in Example 4, 1-(4-fluorophenyl)-6-fluoro-7-(trans-3-amino-2-methyl-1-azetidinyl)-1,4-dihydro-4-oxo-3-quinolinecarboxylic acid, melting point 235°–239° C., is obtained.

Spectroscopic data: $^1$H NMR, δ,J=Hz,[DMSO-TFA]: 8.64 (s, 1H); 8.25 (b, 2H); 8.1 (d, J=13 Hz, 1H); 7.75 (m, 4H); 5.84 (d, J=8 Hz, 1H); 4.25 (m, 2H); 3.81 (m, 2H); 1.31 (d, J=6 Hz, 3H). IR(KBr).-3388, 1724, 1630, 1505 cm$^{-1}$.

EXAMPLE 59

Preparation of
1-(2-fluoroethyl)-6,8-difluoro-7-(trans-3-amino-2-methyl-1-azetidinyl)-1,4-dihydro-4-oxo-3-quinolinecarboxylic acid By a procedure completely analogous to that described in Example 4, 1-(2-fluoroethyl)-6,8-difluoro-7-(trans-3-amino-2-methyl-1-azetidinyl)-1,4-dihydro-4-oxo-3-quinolinecarboxylic acid, melting point 222°–224° C., is obtained.

Spectroscopic data: $^1$H NMR, δ,J=Hz,[DMSO-TFA]: 1.53 (d, J=6 Hz, 3H); 3.7 (m, 1H); 4.27 (m, 2H); 4.7 (m, 3H); 5.0 (m, 2H); 7.9 (d, J=12 Hz, 1H); 8.44 (b, 2H); 8.8 (s, 1H). IR(KBr).-2985, 1632, 1476 cm$^{-1}$.

EXAMPLE 60

Preparation of
1-(2-fluoroethyl)-6-fluoro-7-(trans-3-amino-2-methyl-1-azetidinyl)-1,4-dihydro-4-oxo-3-quinolinecarboxylic acid By a procedure completely analagous to that described in Example 4, 1-(2-fluoroethyl)-6-fluoro-7-(trans-3-amino-2-methyl-1-azetidinyl)-1,4-dihydro-4-oxo-3-quinolinecarboxylic acid, melting point 205°–220° C., is obtained.

Spectroscopic data: $^1$H NMR, δ,J=Hz, [DMSO-TFA]: 1.52 (d, J=6 Hz, 3H); 3.92 (m, 2H); 4.6 (m, 4H); 5.0 (m, 2H); 6.75 (d, J=7 Hz, 1H); 7.9 (d, J=13 Hz, 1H); 8.4 (b, 2H); 8.83 (s, 1H). IR(KBr).-3100, 1631, 1490, 1341 cm$^{-1}$.

EXAMPLE 61

Preparation of
1-(4-fluorophenyl)-6,8-difluoro-7-(trans-3-amino-2-methyl-1-azetidinyl)-1,4-dihydro-4-oxo-3-quinolinecarboxylic acid By a procedure completely analagous to that described in Example 4, 1-(4-fluorophenyl)-6,8-difluoro-7-(trans-3-amino-2-methyl-1-azetidinyl)-1,4-dihydro-4-oxo-3-quinolinecarboxylic acid, melting point 223°–229° C., is obtained.

Spectroscopic data: $^1$H NMR, δ,J=Hz, [DMSO-TFA]: 8.45, (s, 1H); 8.3 (b, 2H); 7.8 (m, 5H); 4.55 (m, 2H); 4.02 (m, 1H); 3.64 (m, 1H); 1.4 (d, J=6 Hz, 3H). IR(KBr).-3420, 1623, 1578, 1472 cm$^{-1}$.

EXAMPLE 62

Preparation of
(3S)-(−)-10-[(2R,3S)-3-amino-2methyl-1-azetidinyl]-9-fluoro-2,3-dihydro-3-methyl-7-oxo-7H-pyrido[1,2,3-de][1,4]benzoxazine-6-carboxylic acid By a procedure completely analagous to that described in Example 4, (3S)-(−)-10-[(2R,3S)-3-amino-2-methyl-1-azetidinyl]-9-fluoro-2,3-dihydro-3-methyl-7-oxo-7H-pyrido[1,2,3-de][1,4]benzoxazine-6-carboxylic acid, melting point 217°–219° C., is obtained.

$[\alpha]_D^{20}$ = −106.8 (c=0.31, 0.5N NaOH)

Spectroscopic data: $^1$H NMR, δ,J=Hz,[DMSO-TFA]: 1.50 (m, 6H); 3.7 (m, 1H); 4.00–5.10 (m, 6H); 7.58 (d, J=14.0 Hz, 1H); 8.35 (b, 3H); 8.92 (s, 1H). IR(KBr).-3425, 2975, 1623, 1472, 1333 cm$^{-1}$.

EXAMPLE 63

Preparation of (3R)-(+)-10-[(2S,3R)-3-amino-2-methyl-1-azetidinyl]-9-fluoro-2,3-dihydro-3-methyl-7-oxo-7H-pyrido[1,2,3-de][1,4]benzoxazine-6-carboxylic acid By a procedure completely analagous to that described in Example 4, (3R)-(+)-10-[(2S,3R)-3-amino-2-methyl-1-azetidinyl]-9-fluoro-2,3-dihydro-3-methyl-7-oxo-7H-pyrido[1,2,3-de][1,4]benzoxazine-6-carboxylic acid, melting point 215°–217° C., is obtained.

$[\alpha]_D^{20}$ = +104.7 (c=0.25, 0.5N NaOH)

Spectroscopic data: $^1$H NMR, δ,J=Hz,[DMSO-TFA]: 1.50 (m, 6H); 3.7 (m, 1H); 4.00–5.10 (m, 6H); 7.58 (d, J=14.0 Hz, 1H); 8.35 (b, 3H); 8.92 (s, 1H). IR(KBr).-3425, 2975, 1623, 1472, 1333 cm$^{-1}$.

EXAMPLE 64

Preparation of
(+)-1-cyclopropyl-6,8-difluoro-7-[(2R,3S)-3-amino-2-methyl-1-azetidinyl]-1,4-dihydro-4-oxo-3-quinolinecarboxylic acid By a procedure completely analagous to that described in Example 4, (+)-1-cyclopropyl-6,8-difluoro-7-[(2R,3S)-3-amino-2-methyl-1-azetidinyl]-1,4-dihydro-4-oxo-3-quinolinecarboxylic acid, melting point 229°–231° C., is obtained.

$[\alpha]_D^{20}$ = +9.4 (c=0.26, 0.5N NaOH)

Spectroscopic data: $^1$H NMR, δ,J=Hz,[DMSO-TFA]: 8.61; (s, 1H); 8.32 (b, 2H); 7.70 (dd, J=13, J=1.5, 1H); 4.76 (m, 2H); 4.09 (m, 2H); 3.72 (m, 1H); 1.53 (d, J=6, 3H); 1.16 (d, J=6, 4H). IR(KBr).-1719, 1630, 1578, 1466, 1402, 1319 cm$^{-1}$.

EXAMPLE 65

Preparation of
(−)-1-cyclopropyl-6,8-difluoro-7-[(2S,3R)-3-amino-2-methyl-1-azetidinyl]-1,4-dihydro-4-oxo-3-quinolinecarboxylic acid By a procedure completely analagous to that described in Example 4, (−)-1-cyclopropyl-6,8-difluoro-7-[(2S,3R)-3-amino-2-methyl-1-azetidinyl]-1,4-dihydro-4-oxo-3-quinolinecarboxylic acid, melting point 231°–233° C., is obtained.

$[\alpha]_D^{20}$ = −10.6 (c=0.27, 0.5N NaOH)

Spectroscopic data: $^1$H NMR,δ,J=Hz,[DMSO-TFA]: 8.61 (s, 1H); 8.32 (b, 2H); 7.70 (dd, J=13, J=1.5, 1H); 4.76 (m, 2H); 4.09 (m, 2H); 3.72 (m, 1H); 1.53 (d, J=6, 3H); 1.16 (d, J=6, 4H). IR(KBr).-1719, 1630, 1578, 1466, 1402, 1319 cm$^{-1}$.

EXAMPLE 66

Preparation of
(−)-1-cyclopropyl-6-fluoro-7-[(2R,3S)-3-amino-2-methyl-1-azetidinyl]-1,4-dihydro-4-oxo-1,8-naphthyridine-3-carboxylic acid By a procedure completely analagous to that described in Example 4, (−)-1-cyclopropyl-6-fluoro-7-[(2R,3S)-3-amino-2-methyl-1-azetidinyl]-1,4-dihydro-4-oxo-1,8-naphthyridine-3-carboxylic acid, melting point 236°–239° C., is obtained.

$[\alpha]_D^{20}$ = −7.0 (c=0.37, 0.5N NaOH)

Spectroscopic data: $^1$H NMR,δ,J=Hz,[DMSO-TFA]: 8.64 (s, 1H); 8.35 (b, 2H); 8 (d, J=13 Hz, 1H); 4.7 (m, 2H); 4.25 (m, 1H); 3.65 (m, 2H); 1.62 (d, J=6 Hz, 3H); 1.1 (m, 4H). IR(KBr).-2943, 1629, 1447 cm$^{-1}$.

EXAMPLE 67

Preparation of
(+)-1-cyclopropyl-6-fluoro-7-[(2S,3R)-3-amino-2-methyl-1-azetidinyl]-1,4-dihydro-4-oxo-1,8-naphthyridine-3-carboxylic acid By a procedure completely analagous to that described in Example 4, (+)-1-cyclopropyl-6-fluoro-7-[(2S,3R)-3-amino-2-methyl-1-azetidinyl]-1,4-dihydro-4-oxo-1,8-naphthyridine-3-carboxylic acid, melting point 236°–239° C., is obtained.

$[\alpha]_D^{20}$ = +7.6 (c=0.42, 0.5N NaOH)

Spectroscopic data: $^1$H NMR,δ,J=Hz,[DMSO-TFA]: 8.64 (s, 1H); 8.35 (b, 2H); 8 (d, J=13 Hz, 1H); 4.7 (m, 2H); 4.25 (m, 1H); 3.65 (m, 2H); 1.62 (d, J=6 Hz, 3H); 1.1 (m, 4H). IR(KBr).-2943, 1629, 1447 cm$^{-1}$.

EXAMPLE 68

Preparation of
(+)-1-cyclopropyl-6-fluoro-7-[(2R,3S)-3-amino-2-methyl-1-azetidinyl]-1,4-dihydro-4-oxo-3-quinolinecarboxylic acid By a procedure completely analagous to that described in Example 4, (+)-1-cyclopropyl-6-fluoro-7-[(2R,3S)-3-amino-2-methyl-1-azetidinyl]-1,4-dihydro-4-oxo-3-quinolinecarboxylic acid, melting point 242°–244° C., is obtained.

$[\alpha]_D^{20} = +13.7$ (c=0.38, 0.5N NaOH)

Spectroscopic data: $^1$H NMR, δ,J=Hz,[DMSO-TFA]: 8.61 (s, 1H); 8.37 (b, 2H); 7.86 (d, J=13, 1H); 7.04 (d, J=8, 1H); 4.53 (m, 2H); 3.92 (m, 3H); 1.54 (d, J=6, 3H); 1.19 (d, J=8, 4H) IR(KBr).-1719, 1629, 1479, 1325 cm$^{-1}$,

EXAMPLE 69

Preparation of
(−)-1-cyclopropyl-6-fluoro-7-[(2S,3R)-3-amino-2-methyl-1-azetidinyl]-1,4-dihydro-4-oxo-3-quinolinecarboxylic acid By a procedure completely analogous to that described in Example 4, (−)-1-cyclopropyl-6-fluoro-7-[(2S,3R)-3-amino-2-methyl-1-azetidinyl]-1,4-dihydro-4-oxo-3-quinolinecarboxylic acid, melting point 242°–244° C., is obtained.

$[\alpha]_D^{20} = -13.3$, (c=0.31, 0.5N NaOH)

Spectroscopic data: $^1$H NMR, δ,J=Hz,[DMSO-TFA]: 8.61 (s, 1H); 8.37 (b, 2H); 7.86 (d, J=13, 1H); 7.04 (d, J=8, 1H); 4.53 (m, 2H); 3.92 (m, 3H); 1.54 (d, J=6, 3H); 1.19 (d, J=8, 4H). IR(KBr).-1719, 1629, 1479, 1325 cm$^{-1}$.

EXAMPLE 70

Preparation of
(3S)-(−)-10-[(2S,3R)-3-amino-2-methyl-1-azetidinyl]-9-fluoro-2,3-dihydro-3-methyl-7-oxo-7H-pyrido[1,2,3-de][1,4]benzoxazine-6-carboxylic acid, melting point 217°–221° C.

$[\alpha]_D^{20} = -30.27$ (c=0.36, 0.5N NaOH)

Spectroscopic data: $^1$H NMR, δ,J=Hz,[DMSO-TFA]: 1.45 (d, J=7.0 Hz, 3H); 1.52 (d, J=6.0 Hz, 3H); 3.66 (m, 1H); 4.00–5.00 (m, 6H); 7.57 (d, J=13.0 Hz, 1H); 8.36 (b, 3H); 8.92 (s, 1H). IR(KBr).-3393, 2962, 1718, 1624, 1529, 1474, 1131, 800 cm$^{-1}$.

EXAMPLE 71

Preparation of
(3R)-(+)-10-[(2R,3S)-3-amino-2-methyl-1-azetidinyl]-9-fluoro-2,3-dihydro-3-methyl-7-oxo-7H-pyrido[1,2,3-de][1,4]benzoxazine-6-carboxylic acid By a procedure completely analogous to that of Example 4, (3R)-(+)-10-[(2R,3S)-3-amino-2-methyl-1-azetidinyl]-9-fluoro-2,3-dihydro-3-methyl-7-oxo-7H-pyrido[1,2,3-de][1,4]benzoxazine-6-carboxylic acid, melting point 217°–219° C., is obtained.

$[\alpha]_D^{20} = +30.60$ (c=0.31, 0.5N NaOH)

Spectroscopic data: $^1$H NMR,δ,J=Hz,[DMSO-TFA]: 1.45 (d, J=7.0 Hz, 3H); 1.52 (d, J=6.0 Hz, 3H); 3.66 (m, 1H); 4.00–5.00 (m, 6H); 7.57 (d, J=13.0 Hz, 1H); 8.36 (b, 3H); 8.92 (s, 1H). IR(KBr).-3393, 2962, 1718, 1624, 1529, 1474, 1131, 800 cm$^{-1}$.

EXAMPLE 72

Preparation of
(3S)-(−)-9-fluoro-2,3-dihydro-3-methyl-10-(3-methyl-3-methylamino-1-azetidinyl)-7-oxo-7H-pyrido[1,2,3-de][1,4]benzoxazine-6-carboxylic acid By a procedure completely analogous to that described in Example 2, (3S)-9-fluoro-2,3-dihydro-3-methyl-10-{3-methyl-3-[N-(methyl)trifluoroacetamido]-1-azetidinyl}-7-oxo-7H-pyrido[1,2,3-de][1,4]benzoxazine-6-carboxylic acid, melting point >300° C., is obtained.

Spectroscopic data: $^1$H NMR, δ,J=Hz,[DMSO]: 1.44 (d, J=6.0 Hz, 3H); 1.62 (s, 3H); 3.00 (s, 3H); 4.00–4.70 (m, 6H); 4.90 (m, 1H); 7.47 (d, J=13.0 Hz, 1H); 8.88 (s, 1H). IR(KBr).-1726, 1686, 1623, 1476, 1465, 1163, 806 cm$^{-1}$.

The above product is hydrolysed with 10% sodium hydroxide to obtain (3S)-(−)-9-fluoro-2,3-dihydro-3-methyl-10-(3-methyl-3-methylamino-1-azetidinyl)-7-oxo-7H-pyrido[1,2,3-de][1,4]benzoxazine-6-carboxylic acid, melting point 288°–289° C. (dec.).

$[\alpha]_D^{20} = -77.4$ (c=0.50, 0.5N NaOH)

Spectroscopic data: $^1$H NMR, δ,J=HZ,[DMSO-TFA]: 1.46 (d, J=6.0 Hz, 3H); 1.60 (s, 3H); 1.60 (s, 3H); 2.65 (s, 3H); 4.10–4.70 (m, 6H); 4.87 (m, 1H); 7.55 (d, J=13.0 Hz, 1H); 8.91 (s, 1H); 9.26 (b, 2H). IR(KBr).-3431, 3331, 2956, 1702, 1624, 1540, 1474, 806 cm$^{-1}$.

EXAMPLE 73

Preparation of
(3R)-(+)-9-fluoro-2,3-dihydro-3-methyl-10-(3-methyl-3-methylamino-1-azetidinyl)-7-oxo-7H-pyrido[1,2,3-de][1,4]benzoxazine-6-carboxylic acid By a procedure completely analogous to that described in Example 2, (3R)-9-fluoro-2,3-dihydro-3-methyl-10-{3-methyl-3-[N-(methyl)trifluoroacetamido]-1-azetidinyl}-7-oxo-7H-pyrido[1,2,3-de][1,4]benzoxazine-6-carboxylic acid, melting point >300° C., is obtained.

Spectroscopic data: $^1$H MNR, δ,J=Hz,[DMSO]: 1.44 (d, J=6.0 Hz, 3H); 1.62 (s, 3H); 3.00 (s, 3H); 4.00–4.70 (m, 6H); 4.90 (m, 1H); 7.47 (d, J=13.0 Hz, 1H); 8.88 (s, 1H). IR(KBr).-1726, 1686, 1623, 1476, 1465, 1163, 806 cm$^{-1}$.

The above product is hydrolysed with 10% sodium hydroxide to yield (3R)-(+)-9-fluoro-2,3-dihydro-3-methyl-10-(3-methyl-3-methylamino-1-azetidinyl)-7-oxo-7H-pyrido[1,2,3-de][1,4]benzoxazine-6-carboxylic acid, melting point 288°–289° C. (dec.).

$[\alpha]_D^{20} = +76.8$ (c=0.52, 0.5N NaOH)

Spectroscopic data: $^1$H NMR, δ,J=Hz,[DMSO-TFA]: 1.46 (d, J=6.0 Hz, 3H); 1.60 (s, 3H); 1.60 (s, 3H); 2.65 (s, 3H); 4.10–4.70 (m, 6H); 4.87 (m, 1H); 7.55 (d, J=13.0 Hz, 1H); 8.91 (s, 1H); 9.26 (b, 2H). IR(KBr).-3431, 3331, 2956, 1702, 1624, 1540, 1474, 806 cm$^{-1}$.

EXAMPLE 74

Preparation
1-cyclopropyl-6-fluoro-7-(3-methyl-3-methylamino-1-azetidinyl)-1,4-dihydro-4-oxo-1,8-naphthyridine-3-carboxylic acid By a procedure completely analogous to that described in Example 2, 1-cyclopropyl-6-fluoro-7-{3-methyl-3-[N-(methyl)trifluoromethylacetamido]-1-azetidinyl}-1,4-dihydro-4-oxo-1,8-naphthyridine-3-carboxylic acid is obtained, which product is then hydrolysed to yield 1-cyclopropyl-6-fluoro-7-(3-methyl-3-methylamino-1-azetidinyl)-1,4-dihydro-4-oxo-1,8-naphthyridine-3-carboxylic acid, melting point 283°–286° C.

Spectroscopic data: $^1$H NMR, δ,J=Hz,[DMSO-TFA]: 1.0 (m, 4H); 1.62 (s, 3H); 2.62 (s, 3H); 3.73 (m, 1H); 4.38 (AB, J=7.5, 4H); 8 (d, J=11.5 Hz, 1H); 8.54 (s, 1H); 9.34 (b, 2H). IR(KBr).-2900, 1639, 1458 cm$^{-1}$.

EXAMPLE 75

Preparation of 1-(1,1-dimethylethyl)-6-fluoro-7-(3-amino-2-methyl-1-azetidinyl)-1,4-dihydro-4-oxo-3-quinolinecarboxylic acid By a procedure completely analogous to that described in Example 4, 1-(1,1-dimethylethyl)-6-fluoro-7-(3-amino-2-methyl-1-azetidinyl)-1,4-dihydro-4-oxo-3-quinolinecarboxylic acid, melting point 243°–248° C., is obtained.

Spectroscopic data: $^1$NMR, δ,J=HZ,[DMSO-TFA]: 8.88 (s, 1H); 8.49 (b, 2H); 7.93 (d, J=13, 1H); 6.85 (d, J=7.6); 4.26 (AB, J=7, 4H); 1.86 (s, 9H); 1.67 (s, 3H). IR(KBr).-3350, 1718, 1612, 1470 cm$^{-1}$.

EXAMPLE 76

Preparation of 1-(1,1-dimethylethyl)-6-fluoro-7-(3-methyl-3-methylamino-1-azetidinyl)-1,4-dihydro-4-oxo-3-quinolinecarboxylic acid By a procedure completely analogous to that described in Example 2, 1-(1,1-dimethylethyl)-6-fluoro-7-{3-methyl-3-[N-(methyl)trifluoroacetamido]-1-azetidinyl}-1,4-dihydro-4-oxo-3-quinolinecarboxylic acid, melting point 260°–263° C., is obtained.

Spectroscopic data: $^1$H NMR, δ,J=Hz,[DMSO-d$_6$]: 8.85 (s, 1H); 7.87 (d, J=12 Hz, 1H); 6.88 (d, J=7, 1H); 4.22 (AB, J=7, 4H); 3.04 (s, 3H); 1.85 (s, 9H); 1.65 (s, 3H). IR(KBr).-1712, 1689, 1632, 1510, 1464, 1151 cm$^{-1}$.

The above product is hydrolysed with 10% sodium hydroxide to yield 1-(1,1-dimethylethyl)-6-fluoro-7-(3-methyl-3-methylamino-1-azetidinyl)-1,4-dihydro-4-oxo-3-quinolinecarboxylic acid, melting point 251°–253° C.

Spectroscopic data: $^1$H NMR, δ,J=Hz,[DMSO-TFA]: 9.28 (b, 2H); 8.87 (s, 1H); 7.90 (d, J=13, 1H); 6.84 (d, J=7, 1H); 4.26 (AB, J=8 Hz, 4H); 2.62 (s, 3H); 1.82 (s, 9H); 1.61 (s, 3H). IR(KBr).-1630, 1608, 1474, 1341 cm$^{-1}$.

EXAMPLE 77

Preparation of 7-(trans-3-amino-2-methyl-1-azetidinyl)-1-(1,1-dimethylethyl)-6-fluoro-1,4-dihydro-4-oxo-3-quinolinecarboxylic acid By a procedure completely analogous to that of Example 2, 7-(trans-3-amino-2-methyl-1-azetidinyl)-1-(1,1-dimethylethyl)-6-fluoro-1,4-dihydro-4-oxo-3-quinolinecarboxylic acid, melting point 225°–227° C., is obtained.

Spectroscopic data: $^1$H NMR, δ,J=Hz,[DMSO-TFA]: 1.50 (d, J=6.0 Hz, 3H); 1.82 (s, 9H); 3.9 (m, 2H); 4.49 (m, 2H); 6.96 (d, J=7.0 Hz, 1H); 7.91 (d, J=13.0 Hz, 1H); 8.31 (b, 3H); 8.86 (s, 1H). IR(KBr).-3387, 3306, 1718, 1630, 1606, 1509, 1405, 1376, 1338 cm$^{-1}$.

EXAMPLE 78

Preparation of 1-(1,1-dimethylethyl)-6-fluoro-7-(trans-2-methyl-3-methylamino-1-azetidinyl)-1,4-dihydro-4-oxo-3-quinolinecarboxylic acid By a procedure completely analogous to that described in Example 2, 1-(1,1-dimethylethyl)-6-fluoro-7-{trans-2-methyl-3-[N-(methyl)trifluoroacetamido]-1-azetidinyl}-1,4-dihydro-4-oxo-3-quinolinecarboxylic acid, melting point 215°–217° C., is obtained.

Spectroscopic data: $^1$H NMR, δ,J=Hz,[DMSO-TFA]: 1.56 (m, 3H); 1.88 (s, 9H); 3.18 (s, 3H); 4.20–5.00 (m, 4H); 6.99 (d, J=7.4 Hz, 1H); 7.96 (d, J=12.6 Hz, 1H); 8.92 (s, 1H). IR(KBr).-1727, 1697, 1630, 1605, 1509, 1468, 1445, 1337, 1194, 1142 cm$^{-1}$.

The above product is hydrolysed with 10% sodium hydroxide to yield 1-(1,1-dimethylethyl)-6-fluoro-7-(trans-2-methyl-3-methylamino-1-azetidinyl)-1,4-dihydro-4-oxo-3-quinolinecarboxylic acid, melting point 194°–195° C.

Spectroscopic data: $^1$H NMR, δ,J=Hz,[DMSO-TFA]: 1.57 (d, J=6.1 Hz, 3H); 1.89 (s, 9H); 2.67 (s, 3H); 3.75–4.20 (m, 2H); 4.63 (m, 2H); 6.96 (d, J=7.0 Hz, 1H); 8.00 (d, J=13.0 Hz, 1H); 8.93 (s, 1H); 9.21 (b, 2H). IR(KBr).-3325, 2931, 1720, 1630, 1604, 1510, 1492, 1403, 1326, 800 cm$^{-1}$.

EXAMPLE 79

Preparation of 1-(1,1-dimethylethyl)-6-fluoro-7-(3-amino-3-methyl-1-azetidinyl)-1,4-dihydro-4-oxo-1,8-naphthyridine-3-carboxylic acid By a procedure completely analogous to that described in Example 15, 1-(1,1-dimethylethyl)-6-fluoro-7-(3-amino-3-methyl-1-azetidinyl)-1,4-dihydro-4-oxo-1,8-naphthyridine-3-carboxylic acid, melting point 230°–234° C. (dec.), is obtained.

Spectroscopic data: $^1$H NMR, δ,J=Hz,[DMSO-TFA]: 8.86 (s, 1H); 8.47 (b, 2H); 8.09 (d, J=13, 1H); 4.39 (AB, J=7, 4H); 1.86 (s, 9H); 1.67 (s, 3H). IR(KBr).-3360, 1630, 1467 cm$^{-1}$.

EXAMPLE 80

Preparation of 7-(trans-3-amino-2-methyl-1-azetidinyl)-6-fluoro-1-(1,1,-dimethylethyl)-1,4-azetidinyl)-6-fluoro-1-(1,1,-dimethylethyl)-1,4-4-oxo-1,8-naphthyridine-3-carboxylic acid By a procedure completely analogous to that described in Example 15, 7-(trans-3-amino-2-methyl-1-azetidinyl)-6-fluoro-1-(1,1,-dimethylethyl)-1,4-dihydro-4-oxo-1,8-naphthyridine-3-carboxylic acid, melting point 223°–225° C., is obtained.

Spectroscopic data: $^1$H NMR, δ,J=Hz,[DMSO-TFA]: 1.61 (d, J=6.2 Hz, 3H); 1.88 (s, 9H); 3.85 (m, 1H); 4.30 (m, 1H); 4.66 (m, 2H); 8.14 (d, J=12.0 Hz, 1H); 8.36 (b, 3H); 8.88 (s, 1H). IR(KBr).-3425, 2975, 1630, 1560, 1466, 1355 cm$^{-1}$.

EXAMPLE 81

Preparation of 1-(1,1-dimethylethyl)-6-fluoro-7-(3-methyl-3-methylamino-1-azetidinyl)-1,4-dihydro-4-oxo-1,8-naphthyridine-3-carboxylic acid By a procedure completely analogous to that described in Example 2, 1-(1,1-dimethylethyl-6-fluoro-7-{3-methyl-3-[N-(methyl)trifluoroacetamido]-1-azetidinyl}-1,4-dihydro-4-oxo-1,8-naphthyridine-3-carboxylic acid, melting point 263°–265° C., is obtained.

Spectroscopic data: $^1$H NMR, δ,J=Hz,[DMSO-TFA]: 8.82 (s, 1H); 7.98 (d, J=11, 1H); 4.34 (AB, J=9, 4H); 3.02 (s, 3H); 1.84 (s, 9H); 1.62 (s, 3H). IR(KBr).-1725, 1696, 1633, 1509, 1458, 1420, 1141 cm$^{-1}$.

The above product is hydrolysed with 10% sodium hydroxide to obtain 1-(1,1-dimethylethyl)-6-fluoro-7-(3-methyl-3-methylamino-1-azetidinyl)-1,4-dihydro-4-oxo-1,8-naphthyridine-3-carboxylic acid, melting point >300° C.

Spectroscopic data: $^1$H NMR, δ,J=Hz,[DMSO-TFA]: 9.24 (b, 2H); 8.82 (s, 1H); 8.0 (d, J=11, 1H); 4.40 (AB, J=9, 4H); 2.62 (s, 3H); 1.82 (s, 9H); 1.62 (s, 3H). IR(KBr).-1629, 1612, 1504, 1442, 1347 cm$^{-1}$.

EXAMPLE 82

Preparation of 1-(1,1-dimethylethyl)-6-fluoro-7-(trans-2-methyl-3-methylamino-1-azetidinyl)-1,4-dihydro-4-oxo-1,8-naphthyridine-3-carboxylic acid By a procedure completely analogous to that described in Example 2, 1-(1,1-dimethylethyl)-6-fluoro-7-{trans-2-methyl-3-[N-(methyl)trifluoroacetamido]-1-azetidinyl}-1,4-dihydro-4-oxo-1,8-naphthyridine-3-carboxylic acid, melting point 224°–226° C., is obtained.

Spectroscopic data: $^1$H NMR, δ,J=Hz,[DMSO-TFA]: 1.62 (m, 3H); 1.82 (s, 9H); 3.12 (m, 3H); 4.30–5.20 (m, 4H); 8.01 (d, J=11.0 Hz, 1H); 8.82 (s, 1H). IR(KBr).-1725, 1693, 1632, 1449, 1196, 1148 cm$^{-1}$.

The above product is hydrolysed with 10% sodium hydroxide to obtain 1-(1,1-dimethylethyl)-6-fluoro-7-(trans-2-methyl-3-methylamino-1-azetidinyl)-1,4-dihydro-4-oxo-1,8-naphthyridine-3-carboxylic acid, melting point 185°–187° C.

Spectroscopic data: $^1$H NMR, δ,J=Hz,[DMSO-TFA]: 1.65 (d, J=6.3 Hz, 3H); 1.90 (s, 9H); 2.67 (s, 3H); 3.86 (m, 1H); 4.20–5.00 (m, 3H); 8.13 (d, J=11.6 Hz, 1H); 8.90 (s, 1H); 9.24 (b, 2H). IR(KBr).-3325, 1728, 1633, 1603, 1504, 1443, 1325 cm$^{-1}$.

EXAMPLE 83

Preparation of the methylsulphonate salt of 6-fluoro-7-(trans-2-methyl-3-amino-1-azetidinyl)-1-cyclopropyl-1,4-dihydro-4-oxo-1,8-naphthyridine-3-carboxylic acid A solution of methanesulphonic acid in ethanol is added to a suspension of 0.6 g of 6-fluoro-7-(trans-2-methyl-3-amino-1-azetidinyl)-1-cyclopropyl-1,4-dihydro-4-oxo-1,8-naphthyridine-3-carboxylic acid in 20 ml of boiling ethanol until the pH is slightly acid (6). After cooling, the precipitated solid is filtered off and washed with cold ethanol and 0.55 g of the methylsulphonate salt of 6-fluoro-7-(trans-2-methyl-3-amino-1-azetidinyl)-1-cyclopropyl-1,4-dihydro-4-oxo-1,8-naphthyridine-3-carboxylic acid, melting point 254°–257° C., is obtained.

Spectroscopic data: $^1$H NMR, δ,J=Hz,[DMSO-d$_6$]: 1.14 (m, 4H); 1.63 (d, J=6 Hz, 3H); 2.3 (s, 3H); 3.5 (m, 2H); 4.33 (m, 1H); 4.64 (m, 1H); 8.06 (d, J=12 Hz, 1H); 8.37 (b, 2H); 8.6 (s, 1H). IR(KBr).-1710, 1648, 1462, 1232, 1162 cm$^{-1}$.

EXAMPLE 84

Preparation of 1-cyclopropyl-6,8-difluoro-7-(3-amino-2,2-dimethyl-1-azetidinyl)-1,4-dihydro-4-oxo-3-quinolinecarboxylic acid By a procedure completely analogous to that described in Example 4, 1-cyclopropyl-6,8-difluoro-7-(3-amino-2,2-dimethyl-1-azetidinyl)-1,4-dihydro-4-oxo-3-quinolinecarboxylic acid, melting point 214°–216° C., is obtained.

Spectroscopic data: $^1$H NMR, δ,J=Hz,[DMSO-d$_6$]: 1.14, (m, 4H); 1.34 (s, 3H); 1.48 (s, 3H); 3.25 (b, 3H); 4.00 (m, 3H); 4.44 (m, 1H); 7.64 (d, J=13.2 Hz,1H); 8.56 (s, 1H). IR(KBr).-3393, 3325, 1725, 1627, 1522, 1449 cm$^{-1}$.

EXAMPLE 85

Preparation of 1-(1,1-dimethylethyl)-6,8-difluoro-7-(3-methyl-3-amino-1-azetidinyl)-1,4-dihydro-4-oxo-3-quinolinecarboxylic acid By a procedure completely analogous to that described in Example 4, 1-(1,1-dimethylethyl)-6,8-difluoro-7-(3-methyl-3-amino-1-azetidinyl)-1,4-dihydro-4-oxo-3-quinolinecarboxylic acid, melting point >280° C., is obtained.

Spectroscopic data: $^1$H NMR, δ,J=Hz,[DMSO-TFA]: 1.65 (s, 3H); 1.8 (s, 9H); 4.48 (m, 4H); 7.8 (d, J=12 Hz, 1H); 8.5 (b, 2H); 8.62 (s, 1H). IR(KBr).-2990, 1647, 1450, 1324 cm$^{-1}$.

EXAMPLE 86

Preparation of 1-(2,4-difluorophenyl)-6-fluoro-7-(3-methyl-3-amino-1-azetidinyl)-1,4-dihydro-4-oxo-1,8-naphthyridine-3-carboxylic acid By a procedure completely analogous to that described in Example 4,1-(2,4-difluorophenyl)-6-fluoro-7-(3-methyl-3-amino-1-azetidinyl)-1,4-dihydro-4-oxo-1,8-naphthyridine-3-carboxylic acid, melting point 244°–248° C., is obtained.

Spectroscopic data: $^1$H NMR, δ,J=Hz,[DMSO-TFA]: 1.53 (s, 3H); 4.15 (m, 4H); 7.31–7.9 (a.c., 3H); 8.10 (d, J=11 Hz, 1H); 8.37 (b, 2H); 8.82 (s, 1H). IR(KBr).-2960, 1636, 1512, 1465 cm$^{-1}$.

EXAMPLE 87

Preparation of (±)-1-(2,4-difluorophenyl)-6-fluoro-7-(trans-2-methyl-3-amino-1-azetidinyl)-1,4-dihydro-4-oxo-1,8-naphthyridine-3-carboxylic acid By a procedure completely analogous to that described in Example 4, (±)-1-(2,4-difluorophenyl)-6-fluoro-7-(trans-2-methyl-3-amino-1-azetidinyl)-1,4-dihydro-4-oxo-1,8-naphthyridine-3-carboxylic acid, melting point 220° C., is obtained.

Spectroscopic data: $^1$H NMR, δ,J=Hz,[DMSO-TFA]: 1.25 (d, J=6 Hz, 3H); 3.72 (m, 1H); 4.25 (m, 3H); 7.15–7.85 (a.c., 3H); 8.14 (d, J=11 Hz, 1H); 8.25 (b, 2H); 8.83 (s, 1H). IR(KBr).-2925, 1632, 1513, 1451 cm$^{-1}$.

EXAMPLE 88

Preparation of 1-cyclopropyl-6-fluoro-7-(3-amino-2,2-dimethyl-1-azetidinyl)-1,4-dihydro-4-oxo-1,8-naphthyridine-3-carboxylic acid By a procedure completely analogous to that described in Example 2, 1-cyclopropyl-6-fluoro-7-(3-amino-2,2-dimethyl-1-azetidinyl)-1,4-dihydro-4-oxo-1,8-naphthyridine-3-carboxylic acid, melting point 190°–195° C., is obtained.

Spectroscopic data: $^1$H NMR, δ,J=Hz,[DMSO-d$_6$]: 1.13 (m, 4H); 1.55 (s, 3H); 1.63 (s, 3H); 3.60 (b, 3H); 3.90 (m, 3H); 4.50 (m, 1H); 7.95 (d, J=11.0 Hz, 1H); 8.53 (s, 1H). IR(KBr).-3393, 3325, 1725, 1630, 1509, 1449 cm$^{-1}$.

EXAMPLE 89

Preparation of (±)-1-(1,1-dimethylethyl)-6,8-difluoro-7-(trans-2-methyl-3-amino-1-azetidinyl)-1,4-dihydro-4-oxo-3-quinolinecarboxylic acid By a procedure completely analogous to that described in Example 4, (±)-1-(1,1-dimethylethyl)-6,8-difluoro-7-(trans-2-methyl-3-amino-1-azetidinyl)-1,4-dihydro-4-oxo-3-quinolinecarboxylic acid, melting point 263°–266° C., is obtained.

Spectroscopic data: $^1$H NMR, δ,J=Hz,[DMSO-TFA]: 1.51 (d, J=6 Hz, 3H); 1.73 (s, 9H); 3.71 (m, 1H); 4.18 (m, 1H); 4.70 (m, 2H); 7.81 (d, J=12 Hz, 1H); 8.33 (b, 2H); 8.96 (s, 1H). IR(KBr).-2955, 1611, 1470, 1326 cm$^1$.

EXAMPLE 90

Preparation of 5-amino-1-cyclopropyl-6,8-difluoro-7-(3-methyl-3-amino-1-azetidinyl)-1,4-dihydro-4-oxo-3-quinolinecarboxylic acid By a procedure completely analogous to that described in Example 4, 5-amino-1-cyclopropyl-6,8-difluoro-7-(3-methyl-3-amino-1-azetidinyl)-1,4-dihydro-4-oxo-3-quinolinecarboxylic acid, melting point 243°–247° C., is obtained.

Spectroscopic data: $^1$H NMR, δ,J=Hz,[DMSO-d$_6$]: 1.04 (m, 4H); 1.59 (s, 3H); 3.9 (m, 1H); 4.35 (m, 4H); 8.42 (s, 1H); 8.48 (b, 4H). IR(KBr).-1718, 1635, 1525, 1432, 1326 cm$^{-1}$.

EXAMPLE 91

Preparation of (±)-8-chloro-1-cyclopropyl-6-fluoro-7-(trans-2-methyl-3-amino-1-azetidinyl)-1,4-dihydro-4-oxo-3-quinolinecarboxylic acid By a procedure completely analogous to that described in Example 4, (±)-8-chloro-1-cyclopropyl-6-fluoro-7-(trans-2-methyl-3-amino-1-azetidinyl)-1,4-dihydro-4-oxo-3-quinolinecarboxylic acid, melting point 226°–230° C., is obtained.

Spectroscopic data: $^1$H NMR, δ,J=Hz,[DMSO-d$_6$-TFA]: 1.11 (m, 4H); 1.54 (d, J=6 Hz, 3H); 3.7 (m, 1H); 4.25 (m, 2H); 5 (d, J=14 Hz, 1H); 8.45 (b, 2H); 8.73 (s, 1H). IR(KBr).-2969, 1625, 1455, 1447 cm$^{-2}$.

EXAMPLE 92

Preparation of 8-chloro-1-cyclopropyl-6-fluoro-7-(3-methyl-3-amino-1-azetidinyl)-1,4-dihydro-4-oxo-3-quinolinecarboxylic acid By a procedure completely analogous to that described in Example 4, 8-chloro-1-cyclopropyl-6-fluoro-7-(3-methyl-3-amino-1-azetidinyl)-1,4-dihydro-4-oxo-3-quinolinecarboxylic acid, melting point 284°–285° C., is obtained.

Spectroscopic data: $^1$H NMR, δ,J=Hz,[DMSO-d$_6$-TFA]: 1.05 (m, 4H); 1.57 (s, 3H); 4.25 (m, 1H); 4.51 (m, 4H); 7.7 (d, J=14 Hz, 1H); 8.43 (b, 2H); 8.70 (s, 1H). IR(KBr).-2945, 1639, 1611, 1444, 1356 cm$^{-1}$.

EXAMPLE 93

Preparation of (±)-8-chloro-1-(2,4-difluorophenyl)-6-fluoro-7-(trans-2-methyl-3-amino-1-azetidinyl)-1,4-dihydro-4-oxo-3-quinolinecarboxylic acid By a procedure completely analogous to that described in Example 4, (±)-8-chloro-1-(2,4-difluorophenyl)-6-fluoro-7-(trans-2-methyl-3-amino-1-azetidinyl)-1,4-dihydro-4-oxo-3-quinolinecarboxylic acid, melting point 182°–186° C., is obtained.

Spectroscopic data: $^1$H NMR, δ,J=Hz,[DMSO-TFA]: 1.35 (d, J=6 Hz, 3H); 3.55 (m, 1H); 3.95 (m, 1H); 4.95 (m, 2H); 7.3 (m, 3H); 7.8 (d, J=13 Hz, 1H); 8.15 (b, 2H); 8.6 (s, 1H). IR(KBr).-2930, 1622, 1509, 1445 cm$^{-1}$.

EXAMPLE 94

Preparation of 8-chloro-1-(2,4-difluorophenyl)-6-fluoro-7-(3-methyl-3-amino-1-azetidinyl)-1,4-dihydro-4-oxo-3-quinolinecarboxylic acid By a procedure completely analogous to that described in Example 4, 8-chloro-1-(2,4-difluorophenyl)-6-fluoro-7-(3-methyl-3-amino-1-azetidinyl)-1,4-dihydro-4-oxo-3-quinolinecarboxylic acid, melting point 254°–258° C., is obtained.

Spectroscopic data: $^1$H NMR, δ,J=Hz,[DMSO-TFA]: 1.53 (s, 3H); 4.47 (m, 4H); 7.56 (m, 3H); 7.89 (d, J=13 Hz, 1H); 8.42 (b, 2H); 8.57 (s, 1H). IR(KBr).-2932, 1623, 1509, 1448 cm$^{-1}$.

EXAMPLE 95

Preparation of (±)-8-chloro-1-(2-fluoroethyl)-6-fluoro-7-(trans-2-methyl-3-amino-1-azetidinyl)-1,4-dihydro-4-oxo-3-quinolinecarboxylic acid By a procedure completely analogous to that described in Example 4, (±)-8-chloro-1-(2-fluoroethyl)-6-fluoro-7-(trans-2-methyl-3-amino-1-azetidinyl-1,4-dihydro-4-oxo-3-quinolinecarboxylic acid, melting point 232°–236° C., is obtained.

Spectroscopic data: $^1$H NMR, δ,J=Hz,[DMSO-TFA]: 1.5 (d, J=6 Hz, 3H); 3.7 (m, 1H); 4 (m, 1H); 4.5 (m, 1H); 5.0 (m, 5H); 7.9 (d, J=13 Hz, 1H); 8.4 (b, 2H); 8.45 (s, 1H). IR(KBr).-2940, 1631, 1439, 1302 cm$^{-1}$.

EXAMPLE 96

Preparation of
8-chloro-1-(2-fluoroethyl)-6-fluoro-7-(3-methyl-3-amino-1-azetidinyl)-1,4-dihydro-4-oxo-3-quinolinecarboxylic acid By a procedure completely analogous to that described in Example 4, 8-chloro-1-(2-fluoroethyl)-6-fluoro-7-(3-methyl-3-amino-1-azetidinyl)-1,4-dihydro-4-oxo-3-quinolinecarboxylic acid, melting point 275°–277° C., is obtained.

Spectroscopic data: $^1$H NMR, $\delta, J=$Hz,[DMSO-TFA]: 1.56 (s, 3H); 4.52 (m, 5H); 5.0 (m, 2H); 5.3 (m, 1H); 7.8 (d, J=13 Hz, 1H); 8.5 (b, 2H); 8.8 (s, 1H). IR(KBr).-2930, 1634, 1611, 1445, 1333 cm$^{-1}$.

EXAMPLE 97

Preparation of
(±)-8-chloro-1-ethyl-6-fluoro-7-(trans-2-methyl-3-amino-1-azetidinyl)-1,4-dihydro-4-oxo-3-quinolinecarboxylic acid By a procedure completely analogous to that described in Example 4, (±)-8-chloro-1-ethyl-6-fluoro-7-(trans-2-methyl-3-amino-1-azetidinyl)-1,4-dihydro-4-oxo-3-quinolinecarboxylic acid, melting point 230°–232° C., is obtained.

Spectroscopic data: $^1$H NMR, $\delta, J=$Hz,[DMSO-TFA]: 1.35 (t, J=7 Hz, 3H); 1.47 (d, J=6 Hz, 3H); 3.68 (m, 1H); 4.0 (m, 1H); 4.6–4.9 (a.c., 4H); 7.84 (d, J=13 Hz, 1H); 8.34 (b, 2H); 8.80 (s, 1H). IR(KBr).-2950, 1630, 1615, 1445 cm$^{-1}$.

EXAMPLE 98

Preparation of
8-chloro-1-ethyl-6-fluoro-7-(3-methyl-3-amino-1-azetidinyl)-1,4-dihydro-4-oxo-3-quinolinecarboxylic acid By a procedure completely analogous to that described in Example 4, 8-chloro-1-ethyl-6-fluoro-7-(3-methyl-3-amino-1-azetidinyl)-1,4-dihydro-4-oxo-3-quinolinecarboxylic acid, melting point 280°–282° C., is obtained.

Spectroscopic data: $^1$H NMR, $\delta, J=$Hz, [DMSO-TFA]: 1.35 (t, J=7 Hz, 3H); 1.58 (s, eH); 4.52 (m, 3H); 4.6 (q, J=7 Hz, 2H); 7.75 (d, J=13 Hz, 1H); 8.44 (b, 2H); 8.75 (s, 1H). IR(KBr).-2930, 1634, 1612, 1445 cm$^-$.

EXAMPLE 99

Preparation of
(±)-8-chloro-6-fluoro-1-(4-fluorophenyl)-7-(trans-2-methyl-3-amino-1-azetidinyl)-1,4-dihydro-4-oxo-3-quinolinecarboxylic acid By a procedure completely analogous to that described in Example 4, (±)-8-chloro-6-fluoro-1-(4-fluorophenyl)-7-(trans-2-methyl-3-amino-1-azetidinyl)-1,4-dihydro-4-oxo-3-quinolinecarboxylic acid, melting point 245°–247° C., is obtained.

Spectroscopic data: $^1$H MNR, $\delta, J=$Hz, [DMSO-TFA]: 1.38 (d, J=6 Hz, 3H); 3.60 (m, 1H); 4.0 (m, 1H); 4.85 (m, 2H); 7.35 (m, 4H); 7.9 (d, J=13 Hz, 1H); 8.30 (b, 2H); 8.48 (s, 1H). IR(KBr).-1727, 1620, 1505, 1432 cm$^{-1}$.

EXAMPLE 100

Preparation of
8-chloro-6-fluoro-1-(4-fluorophenyl)-7-(3-methyl-3-amino-1-azetidinyl)-1,4-dihydro-4-oxo-3-quinolinecarboxylic acid By a procedure completely analogous to that described in Example 4, 8-chloro-6-fluoro-1-(4-fluorophenyl)-7-(3-methyl-3-amino-1-azetidinyl)-1,4-dihydro-4-oxo-3-quinolinecarboxylic acid, melting point 256°–259° C., is obtained.

Spectroscopic data: $^1$H NMR, $\delta, J=$Hz, [DMSO-TFA]: 1.51, (s, 3H); 4.43 (m, 4H); 7.41 (m, 4H); 7.88 (d, J=13 Hz, 1H); 8.36 (b, 2H); 8.46 (s, 1H). IR(KBr).-2940, 1620, 1441 cm$^{-1}$.

EXAMPLE 101

Preparation of
(±)-6-fluoro-1-(2-fluoroethyl)-7-(trans-2-methyl-3-amino-1-azetidinyl)-1,4-dihydro-4-oxo-1,8-naphthyridine-3-carboxylic acid By a procedure completely analogous to that described in Example 4, (±)-6-fluoro-1-(4-fluoroethyl)-7-(trans-2-methyl-3-amino-1-azetidinyl)-1,4-dihydro-4-oxo-1,8-naphthyridine-3-carboxylic acid, melting point 268°–271° C., is obtained.

Spectroscopic data: $^1$H NMR, $\delta, J=$Hz, [DMSO-TFA]: 1.3 (d, J=6 Hz, 3H); 3.6 (m, 1H); 4 (m, 1H); 4.6 (m, 1H); 5.1 (m, 5H); 7.81 (d, J=11.5 Hz, 1H); 8.25 (b, 2H); 8.79 (s, 1H). IR(KBr).-1631, 1445, 1336 cm$^{-1}$.

EXAMPLE 102

Preparation of
6-fluoro-1-(2-fluoroethyl)-7-(3-methyl-3-amino-1-azetidinyl)-1,4-dihydro-4-oxo-1,8-naphthyridine-3-carboxylic acid By a procedure completely analogous to that described in Example 4, 6-fluoro-1-(2-fluoroethyl)-7-(3-methyl-3-amino-1-azetidinyl)-1,4-dihydro-4-oxo-1,8-naphthyridine-3-carboxylic acid, melting point 279°–286° C., is obtained.

Spectroscopic data: $^1$H NMR, $\delta, J=$Hz,[DMSO-TFA]: 1.53 (s, 3H); 4.4 (m, 6H); 5.2 (m, 2H); 8.09 (d, J=11.5 Hz, 1H); 8.23 (b, 2H); 8.8 (s, 1H). IR(KBr).-1633, 1445, 1315 cm$^{-1}$.

EXAMPLE 103

Preparation of
(±)-1-ethyl-6-fluoro-7-(trans-2-methyl-3-amino-1-azetidinyl)-1,4-dihydro-4-oxo-1,8-naphthyridine-3-carboxylic acid By a procedure completely analogous to that described in Example 4, (±)-1-ethyl-6-fluoro-7-(trans-2-methyl-3-amino-1-azetidinyl)-1,4-dihydro-4-oxo-1,8-naphthyridine-3-carboxylic acid, melting point 212°–215° C., is obtained.

Spectroscopic data: $^1$H NMR, $\delta, J=$Hz, [DMSO-TFA]: 1.4 (t, J=7 Hz, 3H); 1.6 (d, J=6 Hz, 3H); 3.8 (m, 1H); 4.3 (m, 1H); 4.6 (m, 4H); 8.1 (d, J=11.5 Hz, 1H); 8.4 (b, 2H); 8.94 (s, 1H). IR(KBr).-1725, 1633, 1472, 1459 cm$^{-1}$.

EXAMPLE 104

Preparation of 1ethyl-6-fluoro-7-(3-methyl-3-amino-1-azetidinyl)-1,4-dihydro-4-oxo-1,8-naphthyridine-3-carboxylic acid By a procedure completely analogous to that described in Example 4, 1-ethyl-6-fluoro-7-(3-methyl-3-amino-1-azetidiny)-1,4-dihydro-4-oxo-1,8-naphthyridine-3-carboxylic acid, melting point 269°–272° C., is obtained.

Spectroscopic data: $^1$H NMR, $\delta, J = $Hz, [DMSO-TFA]: 1.34 (t, J=7 Hz, 3H); 1.63 (s, 3H); 4.36 (m, 6H); 7.89 (d, J=11.5 Hz, 1H); 8.53 (b, 2H); 8.85 (s, 1H). IR(KBr).-16313, 1617, 1484, 1462 cm$^{-1}$.

EXAMPLE 105

Preparation of (±)-6-fluoro-1-(4-fluorophenyl)-7-(trans-2-methyl-3-amino-1-azetidinyl)-1,4-dihydro-4-oxo-1,8-naphthyridine-3-carboxylic acid By a procedure completely analogous to that described in Example 4, (±)-6-fluoro-1-(4-fluorophenyl)-7-(trans-2-methyl-3-amino-1-azetidinyl)-1,4-dihydro-4-oxo-1,8-naphthyridine-3-carboxylic acid, melting point 239°–244° C., is obtained.

Spectroscopic data: $^1$H NMR, $\delta, J = $Hz, [DMSO-TFA]: 1.17 (d, J=6 Hz, 3H); 3.7 (m, 1H); 4.2 (m, 2H); 4.4 (m, 1H); 7.45 (m, 4H); 8.12 (d, J=11.5 Hz, 1H); 8.2 (b, 2H); 8.67 (s, 1H). IR(KBr).-1726, 1630, 1504, 1448 cm$^{-1}$.

EXAMPLE 106

Preparation of 6-fluoro-1-(4-fluorophenyl)-7-(3-methyl-3-amino-1-azetidinyl)-1,4-dihydro-4-oxo-1,8-naphthyridine-3-carboxylic acid By a procedure completely analogous to that described in Example 4, 6-fluoro-1-(4-fluorophenyl)-7-(3-methyl-3-amino-1-azetidinyl)-1,4-dihydro-4-oxo-1,8-naphthyridine-3-carboxylic acid, melting point 258°–260° C., is obtained.

Spectroscopic data: $^1$H NMR, $\delta, J = $Hz, [DMSO-TFA]: 1.52 (s, 3H); 4.12 (m, 4H); 7.4 (m, 4H); 8.1 (d, J=11.5 Hz, 1H); 8.31 (b, 2H); 8.64 (s, 1H). IR(KBr).-2935, 1631, 1460 cm$^{-1}$.

EXAMPLE 107

Preparation of 6-fluoro-1-(2,4-difluorophenyl)-7-(3-amino-1-azetidinyl)-1,4-dihydro-4-oxo-1,8-naphthyridine-3-carboxylic acid By a procedure completely analogous to that described in Example 4, 6-fluoro-1-(2,4-difluorophenyl)-7-(3-amino-1-azetidinyl)-1,4-dihydro-4-oxo-1,8-naphthyridine-3-carboxylic acid, melting point 236°–241° C., is obtained.

Spectroscopic data: $^1$H NMR, $\delta, J = $Hz, [DMSO-d$_6$-TFA]: 4.1 (m, 5H); 7.5 (m, 3H); 8.07 (d, J=11.5 Hz, 1H); 8.23 (b, 2H); 8.8 (s, 1H). IR(KBr).-1632, 1512, 1459 cm$^{-1}$.

EXAMPLE 108

Preparation of the p-toluenesulphonic acid salt of 6-fluoro-1-(2,4-difluorophenyl)-7-(3-amino-1-azetidinyl)-1,4-dihydro-4-oxo-1,8-naphthyridine-3-carboxylic acid A solution of 0.2 g of p-toluenesulphonic acid in 2 ml of ethanol is added to a suspension of 0.34 g of 6-fluoro-1-(2,4-difluorophenyl)-7-(3-amino-1-azetidinyl)-1,4-dihydro-4-oxo-1,8-naphthyridine-3-carboxylic acid in 10 ml of ethanol, the mixture is heated to 50° C. for 30 min, after cooling the solid is collected and 0.37 g of the p-toluenesulphonic acid salt, melting point 185°–187° C., is obtained.

Spectroscopic data: $^1$H NMR, $\delta, J = $Hz, [DMSO-d$_6$]: 2.27 (s, 3H); 4.0 (m, 5H); 7.6 (m, 7H); 8.13 (d, J=11.5 Hz, 1H); 8.2 (b, 2H); 8.84 (s, 1H). IR(KBr).-1728, 1631, 1449 cm$^{-1}$.

EXAMPLE 109

Preparation of (±)-8-chloro-6-fluoro-1-(1,1-dimethylethyl)-7-(trans-2-methyl-3-amino-1-azetidinyl)-1,4-dihydro-4-oxo-3-quinolinecarboxylic acid By a procedure completely analogous to that described in Example 4, (±)-8-chloro-6-fluoro-1-(1,1-dimethylethyl)-7-(trans-2-methyl-3-amino-1-azetidinyl)-1,4-dihydro-4-oxo-3-quinolinecarboxylic acid, melting point 263°–270° C., is obtained.

Spectroscopic data: $^1$H NMR, $\delta, J = $Hz, [DMSO-TFA]: 1.07 (d, J=6 Hz, 3H); 1.78 (s, 9H); 3.72 (m, 1H); 4.0 (m, 1H); 4.9 (m, 2H); 7.8 (d, J=13 Hz, 1H); 8.5 (b, 2H); 8.8 (s, 1H). IR(KBr).-2970, 1630, 1611, 1315 cm$^{-1}$.

EXAMPLE 110

Preparation of 8-chloro-6-fluoro-1-(1,1-dimethylethyl)-7-(3-methyl-3-amino-1-azetidinyl)-1,4-dihydro-4-oxo-3-quinolinecarboxylic acid By a procedure completely analogous to that described in Example 4, 8-chloro-6-fluoro-1-(1,1-dimethylethyl)-7-(3-methyl-3-amino-1-azetidinyl)-1,4-dihydro-4-oxo-3-quinolinecarboxylic acid, melting point 276°–284° C., is obtained.

Spectroscopic data: $^1$NMR, $\delta, J = $Hz, [DMSO-d$_6$-TFA]: 1.55 (s, 3H); 1.74 (s, 9H); 4.45 (m, 4H); 7.83 (d, J=13 Hz, 1H); 8.6 (b, 2H); 8.8 (s, 1H). IR(KBr).-2945, 1634, 1462 cm$^{-1}$.

EXAMPLE 111

Preparation of (−)-1-(2,4-difluorophenyl)-6,8-difluoro-7-[(2S,3R)-3-amino-2-methyl-1-azetidinyl)-1,4-dihydro-4-oxo-3-quinolinecarboxylic acid By a procedure completely analogous to that described in Example 4, (−)-1-(2,4-difluorophenyl)-6,8-difluoro-7-[(2S,3R)-3-amino-2-methyl-1-azetidinyl]-1,4-dihydro-4-oxo-3-quinolinecarboxylic acid, melting point 200°–204° C., is obtained.

$[\alpha]_D^{20} = -14.0$ (c=0.30, 0.5N NaOH)

Spectroscopic data: $^1$H NMR, $\delta, J = $Hz, [DMSO-TFA]: 1.4 (d, J=6 Hz, 3H); 3.65 (m, 1H); 4.1 (m, 1H); 4.6 (m, 2H); 7.81 (m, 4H); 8.34 (b, 2H); 8.61 (s, 1H). IR(KBr).-1619, 1509, 1474 cm$^{-1}$.

BIOLOGICAL ACTIVITY

The antimicrobial pharmacological activity of these compounds was studied according to the references indicated below.

Antimicrobial pharmacological activity (G. L. Daquet and Y. A. Chabbect, *Techniques en bacteriologie*, (Techniques in Bacteriology), Vol 3, Flammarion Médecine-Sciences, Paris 1972, and W. B. Hugo and A. D. Rusell, *Pharmaceutical Microbiology*, Blackwell Scientific Publications, London, 1977.

Culture medium and solvent:
Antibiotic Agar No. 1 (Oxoid CM 327)
Tryptone Soya Broth (Oxoid CM 129)
Ringer physiological solution ¼ (Oxoid BR 52)
Dextrose Agar (BBL 11165)
Microorganisms
"*Bacillus subtilis*" ATCC 6633
"*Citrobacter freundii*" ATCC 112606
"*Enterobacter aerogenes*" ATCC 15038
"*Enterobacter cloacae*" ATCC 23355
"*Bacillus cereus*" ATCC 1178
"*Escherichia coli*" ATCC 10799
"*Escherichia coli*" ATCC 23559
"*Klebsiella pneumoniae*" ATCC 10031
"*Proteus vulgaris*" ATCC 8427
"*Morg. morganii*" ATCC 8019
"*Pseudomonas aeruginosa*" ATCC 9721
"*Pseudomonas aeruginosa*" ATCC 10145
"*Salmonella tiphymurium*" ATCC 14028
"*Salmonella tiphymurium*" ATCC 6539
"*Serratia marcescens*" ATCC 13880
"*Shigella flexnerii*" ATCC 12022
"*Staphylococcus epidermis*" ATCC 155-1
"*Staphylococcus aureus*" ATCC 25178
"*Streptococcus faecalis*" ATCC 10541

Preparation of the inocula

Each of the microorganisms is seeded by streaking in tubes of antibiotic Agar No. 1 and incubated for 20 hours at 37° C. A culture loop is then taken, seeding is performed in Tryptone Soya Broth and the culture is incubated for 20 hours at 37° C. The culture obtained is diluted 4-fold with Ringer's physiological solution so as to obtain a standardized suspension of $10^7$–$10^9$ cfu/ml for each organism.

Preparation of the medium containing the derivatives of general formula I

Starting with a solution of 100 µg/ml in 0.1N sodium hydroxide, each product is diluted in Dextrose Agar (melted beforehand and maintained at 50° C.) by successive dilutions so as to obtain the following concentrations: 64, 32, 16, 8, 4, 2, 1, 0.5, 0.25 and 0.125 µg of derivative/ml of medium.

Each concentration of each product is distributed in Petri dishes 10 cm in diameter, on the basis of 10 ml of medium per dish and the same number of dishes as microorganisms to be tested.

When the medium has cooled, the dishes are seeded with the inocula on the basis of 0.4 ml of inoculum per dish. They are spread with a Driglasky loop and the supernatant is collected. The seeded dishes are incubated at 37° C. for 20 hours.

The results obtained are described in the following tables. The activity of the compounds "in vitro" is compared therein to that of norfloxacin. The concentrations are given in µg/ml.

| MICROORGANISM | Norfloxacin | EXAMPLES | | | | | | | | | | |
|---|---|---|---|---|---|---|---|---|---|---|---|---|
| | | 1 | 2 | 3 | 4 | 5 | 6 | 7 | 8 | 9 | 10 | 11 |
| *Bacillus subtilis* ATCC 6633 | 0.25 | ≦0.03 | 0.12 | 0.06 | 0.06 | <0.03 | ≦0.03 | ≦0.03 | 0.06 | ≦0.03 | ≦0.03 | 0.12 |
| *Bacillus cereus* ATCC 11778 | 1.0 | 0.06 | 0.50 | 0.25 | 0.25 | 0.06 | 0.06 | 0.25 | 0.50 | 0.06 | 0.06 | 0.25 |
| *Strep. faecalis* ATCC 10541 | 1.0 | 2.00 | 1.00 | 1.00 | 2.00 | 1.00 | 2.00 | 2.00 | 4.00 | 0.25 | 0.25 | 0.50 |
| *Staph. aureus* ATCC 25178 | 2.0 | 0.06 | 0.50 | 0.25 | 0.25 | 0.12 | 0.12 | 0.25 | 0.50 | 0.06 | 0.12 | 0.50 |
| *Staph. epidermidis* ATCC 155-1 | 1.0 | 0.06 | 0.50 | 0.25 | 0.25 | 0.06 | 0.06 | 0.25 | 1.00 | 0.06 | 0.12 | 0.25 |
| *Ps. aeruginosa* ATCC 9721 | 0.5 | 2.00 | 1.00 | 1.00 | 4.00 | 2.00 | 2.00 | 3.00 | 2.00 | 0.25 | 0.25 | 0.50 |
| *Ps. aeruginosa* ATCC 10145 | 1.0 | 2.00 | 2.00 | 2.00 | 4.00 | 2.00 | 2.00 | 3.00 | 4.00 | 0.25 | 0.25 | 1.00 |
| *Citr. freundii* ATCC 11606 | 0.25 | 0.25 | 0.12 | 0.12 | 0.25 | 0.25 | 0.12 | 2.00 | 0.25 | ≦0.03 | ≦0.03 | 0.25 |
| *Morg. morganii* ATCC 8019 | 0.12 | 0.25 | 0.12 | 0.06 | 0.25 | 0.25 | 0.25 | 1.00 | 0.50 | ≦0.03 | ≦0.03 | 0.12 |
| *Proteus vulgaris* ATCC 8427 | 0.06 | 0.06 | 1.00 | 0.25 | 0.50 | 0.12 | 0.06 | 1.00 | 1.00 | 0.06 | 0.06 | 1.00 |
| *Kleb. pneumoniae* ATCC 10031 | 0.03 | ≦0.03 | 0.12 | 0.06 | 0.25 | ≦0.03 | ≦0.03 | 0.25 | 0.06 | ≦0.03 | ≦0.03 | 0.12 |
| *Sal. typhimurium* ATCC 14028 | 0.25 | 0.50 | 0.25 | 0.12 | 0.50 | 0.25 | 0.25 | 2.00 | 0.50 | ≦0.03 | ≦0.03 | 0.25 |
| *Sal. typhi* ATCC 6539 | 0.06 | 0.25 | 0.12 | 0.12 | 0.50 | 0.25 | 0.12 | 1.00 | 0.50 | ≦0.03 | ≦0.03 | 0.25 |
| *Escherichia coli* ATCC 10799 | 0.25 | 0.50 | 0.25 | 0.12 | 0.50 | 0.25 | 0.25 | 2.00 | 0.50 | ≦0.03 | ≦0.03 | 0.25 |
| *Escherichia coli* ATCC 23559 | 0.06 | 0.12 | 0.12 | 0.06 | 0.25 | 0.06 | 0.12 | 1.00 | 0.25 | ≦0.03 | ≦0.03 | 0.12 |
| *Ent. aerogenes* ATCC 15038 | 0.25 | 0.25 | 0.25 | 0.12 | 0.25 | 0.25 | 0.25 | 2.00 | 0.50 | ≦0.03 | ≦0.03 | 0.25 |
| *Ent. cloacae* ATCC 23355 | 0.06 | 0.12 | 0.12 | 0.12 | 0.25 | 0.12 | 0.12 | 2.00 | 0.12 | ≦0.03 | ≦0.03 | 0.25 |
| *Serr. marcescens* ATCC 13880 | 0.50 | 0.25 | 0.25 | 0.25 | 1.00 | 1.00 | 0.50 | 4.00 | 1.00 | 0.06 | 0.12 | 0.50 |
| *Shigella flexnerii* ATCC 12022 | 0.12 | 0.12 | 0.06 | 0.06 | 0.25 | 0.06 | 0.06 | 0.25 | 0.12 | ≦0.03 | ≦0.03 | 0.12 |

-continued

| MICROORGANISM | Norfloxacin | EXAMPLES |||||||||||
| | | 12 | 13 | 14 | 15 | 16 | 17 | 18 | 19 | 27 | 28 | 29 |
|---|---|---|---|---|---|---|---|---|---|---|---|---|
| *Bacillus subtilis* ATCC 6633 | 0.25 | 0.06 | ≦0.03 | 0.06 | ≦0.03 | ≦0.03 | 0.06 | ≦0.03 | 0.06 | ≦0.03 | ≦0.03 | ≦0.03 |
| *Bacillus cereus* ATCC 11778 | 1.0 | 0.12 | 1.00 | 0.50 | 0.12 | 0.06 | 0.12 | 0.06 | 0.50 | ≦0.03 | 1.0 | 1.0 |
| *Strep. faecalis* ATCC 10541 | 1.0 | 1.00 | 1.00 | 1.00 | 0.25 | 0.25 | 0.12 | 2.00 | 2.00 | 2.0 | 1.0 | 1.0 |
| *Staph. aureus* ATCC 25178 | 2.0 | 0.12 | 0.12 | 0.50 | 0.25 | 0.12 | 0.12 | 0.12 | 0.25 | 0.06 | 0.12 | 0.12 |
| *Staph. epidermidis* ATCC 155-1 | 1.0 | 0.12 | 0.12 | 0.25 | 0.12 | 0.12 | 0.06 | 0.12 | 0.12 | 0.06 | 0.06 | 0.06 |
| *Ps. aeruginosa* ATCC 9721 | 0.5 | 2.00 | 2.00 | 4.00 | 0.50 | 0.25 | 0.25 | 2.00 | 2.00 | 1.00 | 4.0 | 4.0 |
| *Ps. aeruginosa* ATCC 10145 | 1.0 | 2.00 | 2.00 | 2.00 | 0.50 | 0.50 | 0.25 | 4.00 | 4.00 | 2.00 | 2.0 | 2.0 |
| *Citr. freundii* ATCC 11606 | 0.25 | 0.25 | 0.50 | 1.00 | 0.06 | ≦0.03 | 0.06 | 0.12 | 0.50 | 0.12 | 0.12 | 0.12 |
| *Morg. morganii* ATCC 8019 | 0.12 | 0.25 | 0.50 | 0.50 | 0.06 | ≦0.03 | 0.06 | 0.12 | 0.25 | 0.12 | 0.25 | 0.25 |
| *Proteus vulgaris* ATCC 8427 | 0.06 | 0.12 | 0.25 | 0.25 | 0.12 | 0.06 | 0.25 | 0.25 | 0.50 | 0.12 | 0.25 | 0.25 |
| *Kleb. pneumoniae* ATCC 10031 | 0.03 | 0.06 | 0.12 | 0.12 | ≦0.03 | ≦0.03 | ≦0.03 | ≦0.03 | 0.12 | 0.03 | 0.06 | 0.06 |
| *Sal. typhimurium* ATCC 14028 | 0.25 | 0.12 | 0.50 | 1.00 | 0.06 | ≦0.03 | 0.06 | 0.25 | 0.25 | 0.25 | 0.25 | 0.25 |
| *Sal. typhi* ATCC 6539 | 0.06 | 0.06 | 0.25 | 0.25 | ≦0.03 | ≦0.03 | ≦0.03 | 0.06 | 0.12 | 0.03 | 0.06 | 0.06 |
| *Escherichia coli* ATCC 10799 | 0.25 | 0.50 | 1.00 | 1.00 | 0.06 | ≦0.03 | 0.06 | 0.25 | 0.50 | 0.12 | 0.25 | 0.25 |
| *Escherichia coli* ATCC 23559 | 0.06 | 0.25 | 0.12 | 0.25 | ≦0.03 | ≦0.03 | ≦0.03 | 0.06 | 0.12 | 0.06 | 0.06 | 0.06 |
| *Ent. aerogenes* ATCC 15038 | 0.25 | 0.50 | 0.50 | 1.00 | ≦0.03 | ≦0.03 | 0.06 | 0.25 | 0.25 | 0.12 | 0.50 | 0.50 |
| *Ent. cloacae* ATCC 23355 | 0.06 | 0.12 | 0.25 | 0.50 | ≦0.03 | ≦0.03 | ≦0.03 | 0.06 | 0.50 | 0.12 | 0.12 | 0.12 |
| *Serr. marcescens* ATCC 13880 | 0.50 | 0.50 | 1.00 | 1.00 | 0.06 | 0.06 | 0.12 | 0.25 | 0.50 | 0.25 | 1.0 | 1.0 |
| *Shigella flexnerii* ATCC 12022 | 0.12 | 0.06 | 0.12 | 0.06 | ≦0.03 | ≦0.03 | ≦0.03 | 0.06 | 0.25 | 0.06 | 0.06 | 0.06 |

| MICROORGANISM | Norfloxacin | EXAMPLES |||||||||||
| | | 30 | 31 | 32 | 33 | 34 | 35 | 36 | 37 | 38 | 39 | 40 |
|---|---|---|---|---|---|---|---|---|---|---|---|---|
| *Bacillus subtilis* ATCC 6633 | 0.25 | 0.06 | 0.06 | 0.06 | 0.06 | ≦0.03 | ≦0.03 | 0.06 | 0.12 | 0.12 | 0.06 | ≦0.03 |
| *Bacillus cereus* ATCC 11778 | 1.0 | 0.50 | 0.50 | 1.00 | 0.25 | 0.12 | 0.06 | 1.00 | 0.25 | 0.50 | 1.00 | 0.12 |
| *Strep. faecalis* ATCC 10541 | 1.0 | 2.00 | 4.00 | 1.00 | 0.25 | 0.25 | 0.50 | 4.00 | 2.00 | 8.00 | 8.00 | 1.00 |
| *Staph. aureus* ATCC 25178 | 2.0 | 0.50 | 0.50 | 0.25 | 0.12 | 0.12 | 0.06 | 0.50 | 0.25 | 1.00 | 1.00 | 0.12 |
| *Staph. epidermidis* ATCC 155-1 | 1.0 | 0.25 | 0.50 | 0.25 | 0.12 | 0.06 | ≦0.03 | 0.50 | 0.25 | 0.50 | 0.50 | 0.12 |
| *Ps. aeruginosa* ATCC 9721 | 0.5 | 4.00 | 8.00 | 2.00 | 0.50 | 0.50 | 0.50 | 4.00 | 2.00 | 8.00 | 8.00 | 2.00 |
| *Ps. aeruginosa* ATCC 10145 | 1.0 | 8.00 | 8.00 | 2.00 | 0.50 | 0.50 | 0.50 | 4.00 | 4.00 | 8.00 | 8.00 | 2.00 |
| *Citr. freundii* ATCC 11606 | 0.25 | 1.00 | 1.00 | 0.25 | 0.12 | ≦0.03 | ≦0.03 | 0.12 | 0.25 | 1.00 | 1.00 | 0.06 |
| *Morg. morganii* ATCC 8019 | 0.12 | 1.00 | 1.00 | 1.00 | 0.25 | 0.06 | 0.06 | 0.50 | 0.50 | 1.00 | 1.00 | 0.06 |
| *Proteus vulgaris* ATCC 8427 | 0.06 | 1.00 | 2.00 | 1.00 | 0.25 | 0.12 | 0.12 | 1.00 | 0.50 | 0.50 | 0.50 | 0.25 |
| *Kleb. pneumoniae* ATCC 10031 | 0.03 | 1.00 | 1.00 | 0.06 | 0.12 | ≦0.03 | ≦0.03 | 0.06 | 0.06 | 0.50 | 0.50 | ≦0.03 |
| *Sal. typhimurium* ATCC 14028 | 0.25 | 1.00 | 1.00 | 0.25 | 0.12 | 0.06 | ≦0.03 | 0.12 | 0.25 | 1.00 | 1.00 | 0.06 |
| *Sal. typhi* ATCC 6539 | 0.06 | 1.00 | 1.00 | 0.12 | 0.06 | ≦0.03 | ≦0.03 | 0.06 | 0.12 | 1.00 | 1.00 | ≦0.03 |
| *Escherichia coli* ATCC 10799 | 0.25 | 1.00 | 1.00 | 0.12 | 0.06 | 0.06 | ≦0.03 | 0.12 | 0.25 | 1.00 | 2.00 | 0.06 |
| *Escherichia coli* ATCC 23559 | 0.06 | 0.25 | 0.50 | 0.12 | 0.06 | ≦0.03 | ≦0.03 | 0.06 | 0.12 | 0.50 | 0.50 | ≦0.03 |
| *Ent. aerogenes* ATCC 15038 | 0.25 | 1.00 | 1.00 | 0.50 | 0.25 | 0.06 | ≦0.03 | 0.50 | 0.25 | 1.00 | 1.00 | 0.06 |
| *Ent. cloacae* ATCC 23355 | 0.06 | 0.50 | 1.00 | 0.12 | 0.06 | ≦0.03 | ≦0.03 | 0.12 | 1.00 | 0.50 | 0.50 | ≦0.03 |
| *Serr. marcescens* ATCC 13880 | 0.50 | 4.00 | 4.00 | 2.00 | 0.50 | 0.25 | 0.12 | 1.00 | 1.00 | 1.00 | 2.00 | 0.50 |
| *Shigella flexnerii* ATCC 12022 | 0.12 | 0.25 | 0.50 | 0.12 | 0.06 | ≦0.03 | ≦0.03 | 0.06 | 0.12 | 0.50 | 1.00 | ≦0.03 |

-continued

| MICROORGANISM | Norfloxacin | EXAMPLES |||||||||||
| --- | --- | --- | --- | --- | --- | --- | --- | --- | --- | --- | --- | --- |
| | | 41 | 42 | 43 | 44 | 45 | 46 | 47 | 49 | 50 | 51 | 52 |
| *Bacillus subtilis* ATCC 6633 | 0.25 | 0.06 | 0.06 | ≦0.03 | 0.06 | ≦0.03 | ≦0.03 | ≦0.03 | ≦0.03 | 0.06 | 0.06 | ≦0.03 |
| *Bacillus cereus* ATCC 11778 | 1.0 | 0.12 | 0.12 | 0.06 | 0.25 | 0.25 | 0.25 | 0.25 | ≦0.03 | 0.25 | 0.25 | 0.12 |
| *Strep. faecalis* ATCC 10541 | 1.0 | 0.50 | 1.00 | 0.50 | 1.00 | 2.00 | 2.00 | 2.00 | 0.06 | 1.00 | 2.00 | 2.0 |
| *Staph. aureus* ATCC 25178 | 2.0 | 0.12 | 0.12 | 0.12 | 0.25 | 0.25 | 0.25 | 0.25 | ≦0.03 | 0.25 | 0.25 | 0.12 |
| *Staph. epidermidis* ATCC 155-1 | 1.0 | 0.12 | 0.12 | 0.06 | 0.12 | 0.12 | 0.25 | 0.25 | ≦0.03 | 0.25 | 0.25 | 0.12 |
| *Ps. aeruginosa* ATCC 9721 | 0.5 | 2.00 | 1.00 | 0.50 | 1.00 | 1.00 | 4.00 | 4.00 | 0.12 | 1.00 | 2.00 | 2.0 |
| *Ps. aeruginosa* ATCC 10145 | 1.0 | 2.00 | 1.00 | 0.50 | 2.00 | 2.00 | 8.00 | 4.00 | 0.25 | 2.00 | 2.00 | 2.0 |
| *Citr. freundii* ATCC 11606 | 0.25 | 0.06 | 0.12 | 0.06 | 0.12 | 0.06 | 0.50 | 0.50 | ≦0.03 | 0.06 | 0.06 | 0.06 |
| *Morg. morganii* ATCC 8019 | 0.12 | 0.12 | 0.12 | ≦0.03 | 0.12 | 0.06 | 0.50 | 0.50 | ≦0.03 | 0.06 | 0.50 | 0.12 |
| *Proteus vulgaris* ATCC 8427 | 0.06 | 0.25 | 0.25 | 0.06 | 0.50 | 0.25 | 0.25 | 0.25 | 0.06 | 0.25 | 0.25 | 0.25 |
| *Kleb. pneumoniae* ATCC 10031 | 0.03 | 0.12 | 0.12 | ≦0.03 | ≦0.03 | ≦0.03 | ≦0.03 | 0.25 | ≦0.03 | 0.06 | 0.06 | ≦0.03 |
| *Sal. typhimurium* ATCC 14028 | 0.25 | 0.25 | 0.12 | ≦0.03 | 0.12 | 0.06 | 0.50 | 0.50 | ≦0.03 | 0.06 | 0.12 | 0.12 |
| *Sal. typhi* ATCC 6539 | 0.06 | 0.12 | 0.06 | ≦0.03 | 0.06 | ≦0.03 | 0.25 | 0.50 | ≦0.03 | 0.06 | 0.06 | ≦0.03 |
| *Escherichia coli* ATCC 10799 | 0.25 | 0.12 | 0.12 | ≦0.03 | 0.12 | 0.06 | 0.50 | 0.50 | ≦0.03 | 0.06 | 0.12 | 0.12 |
| *Escherichia coli* ATCC 23559 | 0.06 | 0.06 | 0.06 | ≦0.03 | 0.06 | 0.06 | 0.25 | 0.25 | ≦0.03 | 0.06 | 0.06 | 0.06 |
| *Ent. aerogenes* ATCC 15038 | 0.25 | 0.25 | 0.25 | ≦0.03 | 0.12 | 0.06 | 0.50 | 0.50 | ≦0.03 | 0.06 | 0.06 | 0.12 |
| *Ent. cloacae* ATCC 23355 | 0.06 | 0.06 | 0.06 | ≦0.03 | 0.06 | ≦0.03 | 0.25 | 0.25 | ≦0.03 | 0.06 | 0.06 | 0.12 |
| *Serr. marcescens* ATCC 13880 | 0.50 | 0.25 | 0.50 | 0.25 | 0.50 | 0.25 | 1.00 | 1.00 | 0.06 | 0.25 | 0.25 | 0.50 |
| *Shigella flexnerii* ATCC 12022 | 0.12 | 0.06 | 0.06 | ≦0.03 | 0.06 | ≦0.03 | 0.25 | 0.25 | ≦0.03 | 0.06 | 0.06 | 0.06 |

| MICROORGANISM | Norfloxacin | EXAMPLES |||||||||||
| --- | --- | --- | --- | --- | --- | --- | --- | --- | --- | --- | --- | --- |
| | | 53 | 54 | 55 | 56 | 57 | 58 | 59 | 60 | 61 | 62 | 63 |
| *Bacillus subtilis* ATCC 6633 | 0.25 | ≦0.03 | 0.06 | 0.12 | 0.06 | 0.03 | 0.06 | 0.12 | 0.25 | 0.12 | 0.12 | 0.12 |
| *Bacillus cereus* ATCC 11778 | 1.0 | 0.25 | 0.25 | 1.0 | 0.12 | 0.25 | 0.25 | 0.50 | 1.0 | 0.25 | 0.50 | 0.25 |
| *Strep. faecalis* ATCC 10541 | 1.0 | 4.0 | 1.0 | 2.0 | 1.0 | 1.0 | 0.50 | 2.0 | 2.0 | 2.0 | 1.0 | 2.0 |
| *Staph. aureus* ATCC 25178 | 2.0 | 0.25 | 0.25 | 1.0 | 0.12 | 0.12 | 0.25 | 0.50 | 1.0 | 0.25 | 0.25 | 0.5 |
| *Staph. epidermidis* ATCC 155-1 | 1.0 | 0.25 | 0.12 | 0.25 | 0.12 | 0.12 | 0.25 | 0.50 | 1.0 | 0.12 | 0.25 | 0.25 |
| *Ps. aeruginosa* ATCC 9721 | 0.5 | 4.0 | 1.0 | 2.0 | 1.0 | 1.0 | 1.0 | 1.0 | 2.0 | 2.0 | 2.0 | 2.0 |
| *Ps. aeruginosa* ATCC 10145 | 1.0 | 2.0 | 1.0 | 2.0 | 1.0 | 2.0 | 1.0 | 1.0 | 2.0 | 2.0 | 4.0 | 4.0 |
| *Citr. freundii* ATCC 11606 | 0.25 | 0.25 | 0.06 | 0.25 | 0.12 | 0.06 | 0.12 | 0.06 | 0.25 | 0.12 | 0.25 | 0.12 |
| *Morg. morganii* ATCC 8019 | 0.12 | 0.25 | 0.06 | 0.25 | 0.25 | 0.25 | 0.06 | 0.06 | 0.12 | 0.25 | 0.12 | 0.12 |
| *Proteus vulgaris* ATCC 8427 | 0.06 | 0.25 | 0.25 | 1.0 | 0.50 | 0.50 | 0.25 | 0.50 | 2.0 | 0.50 | 0.50 | 0.50 |
| *Kleb. pneumoniae* ATCC 10031 | 0.03 | ≦0.03 | ≦0.03 | 0.06 | 0.06 | ≦0.03 | ≦0.03 | ≦0.03 | 0.12 | 0.12 | 0.06 | 0.03 |
| *Sal. typhimurium* ATCC 14028 | 0.25 | 0.25 | 0.12 | 0.12 | 0.12 | 0.50 | 0.06 | 0.12 | 0.50 | 0.25 | 0.50 | 0.50 |
| *Sal. typhi* ATCC 6539 | 0.06 | 0.12 | ≦0.03 | 0.12 | 0.06 | ≦0.03 | <0.03 | 0.06 | 0.25 | 0.12 | 0.25 | 0.50 |
| *Escherichia coli* ATCC 10799 | 0.25 | 0.12 | 0.12 | 0.25 | 0.12 | ≦0.03 | 0.12 | ≦0.03 | 0.25 | 0.12 | 0.25 | 0.50 |
| *Escherichia coli* ATCC 23559 | 0.06 | 0.12 | 0.06 | 0.12 | 0.06 | 0.06 | 0.06 | 0.06 | 0.12 | 0.12 | 0.25 | 0.25 |
| *Ent. aerogenes* ATCC 15038 | 0.25 | 0.12 | 0.06 | 0.25 | 0.12 | 0.06 | 0.06 | 0.12 | 0.25 | 0.12 | 0.50 | 0.25 |
| *Ent. cloacae* ATCC 23355 | 0.06 | 0.12 | 0.06 | 0.12 | 0.06 | 0.06 | 0.06 | 0.06 | 0.12 | 0.12 | 0.25 | 0.25 |
| *Serr. marcescens* ATCC 13880 | 0.50 | 0.50 | 0.12 | 0.25 | 0.50 | 1.0 | 0.50 | 0.50 | 0.50 | 0.50 | 0.50 | 0.50 |
| *Shigella flexnerii* ATCC 12022 | 0.12 | 0.06 | ≦0.03 | 0.06 | 0.12 | ≦0.03 | ≦0.03 | 0.06 | 0.12 | 0.12 | 0.12 | 0.12 |

-continued

| MICROORGANISM | Norfloxacin | 64 | 65 | 66 | 67 | 68 | 69 | 70 | 71 | 72 | 73 | 74 |
|---|---|---|---|---|---|---|---|---|---|---|---|---|
| *Bacillus subtilis* ATCC 6633 | 0.25 | 0.12 | ≦0.03 | 0.06 | ≦0.03 | 0.25 | 0.06 | ≦0.03 | 0.12 | ≦0.03 | 0.06 | ≦0.03 |
| *Bacillus cereus* ATCC 11778 | 1.0 | 0.50 | 0.06 | 0.25 | 0.12 | 1.0 | 0.50 | 0.06 | 0.25 | 0.25 | 0.50 | 0.06 |
| *Strep. faecalis* ATCC 10541 | 1.0 | 2.0 | 0.25 | 2.0 | 1.0 | 2.0 | 1.00 | 0.12 | 1.00 | 0.50 | 1.0 | 0.25 |
| *Staph. aureus* ATCC 25178 | 2.0 | 0.25 | ≦0.03 | 0.50 | 0.12 | 1.0 | 0.50 | ≦0.03 | 0.12 | 0.25 | 0.50 | 0.12 |
| *Staph. epidermidis* ATCC 155-1 | 1.0 | 0.25 | ≦0.03 | 0.25 | 0.12 | 1.0 | 0.50 | ≦0.03 | 0.12 | 0.12 | 0.25 | 0.12 |
| *Ps. aeruginosa* ATCC 9721 | 0.5 | 2.0 | 0.25 | 2.0 | 0.50 | 4.0 | 2.00 | 0.25 | 1 | 0.50 | 1.0 | 0.25 |
| *Ps. aeruginosa* ATCC 10145 | 1.0 | 4.0 | 0.25 | 2.0 | 1.00 | 4.0 | 4.00 | 0.25 | 2 | 0.50 | 2.0 | 0.50 |
| *Citr. freundii* ATCC 11606 | 0.25 | 0.25 | ≦0.03 | 0.12 | 0.06 | 0.50 | 0.12 | ≦0.03 | 0.12 | 0.06 | 0.12 | ≦0.03 |
| *Morg. morganii* ATCC 8019 | 0.12 | 0.25 | ≦0.03 | 0.25 | 0.06 | 0.50 | 0.25 | ≦0.03 | 0.12 | ≦0.03 | 0.12 | ≦0.03 |
| *Proteus vulgaris* ATCC 8427 | 0.06 | 0.50 | 0.06 | 0.50 | 0.25 | 1.0 | 0.50 | 0.06 | 0.25 | 0.25 | 0.50 | 0.06 |
| *Kleb. pneumoniae* ATCC 10031 | 0.03 | 0.12 | ≦0.03 | 0.06 | ≦0.03 | 0.25 | 0.06 | ≦0.03 | 0.12 | ≦0.03 | 0.06 | ≦0.03 |
| *Sal. typhimurium* ATCC 14028 | 0.25 | 0.50 | ≦0.03 | 0.50 | 0.25 | 0.50 | 0.25 | ≦0.03 | 0.12 | 0.06 | 0.12 | ≦0.03 |
| *Sal. typhi* ATCC 6539 | 0.06 | 0.25 | ≦0.03 | 0.12 | 0.06 | 0.50 | 0.12 | ≦0.03 | 0.12 | ≦0.03 | 0.06 | ≦0.03 |
| *Escherichia coli* ATCC 10799 | 0.25 | 0.25 | ≦0.03 | 0.25 | 0.06 | 0.50 | 0.25 | ≦0.03 | 0.12 | 0.12 | 0.25 | ≦0.03 |
| *Escherichia coli* ATCC 23559 | 0.06 | 0.25 | ≦0.03 | 0.12 | 0.03 | 0.25 | 0.06 | ≦0.03 | 0.12 | ≦0.03 | 0.06 | ≦0.03 |
| *Ent. aerogenes* ATCC 15038 | 0.25 | 0.25 | ≦0.03 | 0.12 | 0.03 | 0.50 | 0.06 | ≦0.03 | 0.12 | 0.06 | 0.12 | ≦0.03 |
| *Ent. cloacae* ATCC 23355 | 0.06 | 0.25 | ≦0.03 | 0.12 | 0.03 | 0.25 | 0.06 | ≦0.03 | 0.12 | ≦0.03 | 0.06 | ≦0.03 |
| *Serr. marcescens* ATCC 13880 | 0.50 | 0.50 | 0.06 | 0.50 | 0.25 | 1.0 | 0.50 | 0.12 | 1.0 | 0.12 | 0.50 | 0.06 |
| *Shigella flexnerii* ATCC 12022 | 0.12 | 0.25 | ≦0.03 | 0.12 | ≦0.03 | 0.25 | 0.06 | ≦0.03 | 0.12 | ≦0.03 | 0.06 | ≦0.03 |

| MICROORGANISM | Norfloxacin | 75 | 76 | 77 | 78 | 79 | 80 | 81 | 82 | 83 | 84 | 85 |
|---|---|---|---|---|---|---|---|---|---|---|---|---|
| *Bacillus subtilis* ATCC 6633 | 0.25 | 0.06 | 0.06 | 0.06 | 0.12 | ≦0.03 | ≦0.03 | ≦0.03 | ≦0.03 | ≦0.03 | ≦0.03 | 0.12 |
| *Bacillus cereus* ATCC 11778 | 1.0 | 0.50 | 0.25 | 0.25 | 0.50 | 0.12 | 0.06 | 0.12 | 0.06 | 0.06 | 0.12 | 0.50 |
| *Strep. faecalis* ATCC 10541 | 1.0 | 0.50 | 1.00 | 0.50 | 1.00 | 0.25 | 0.25 | 0.25 | 0.25 | 0.25 | 0.50 | 2.00 |
| *Staph. aureus* ATCC 25178 | 2.0 | 0.50 | 0.25 | 0.25 | 0.50 | 0.12 | 0.06 | 0.06 | ≦0.03 | 0.12 | 0.12 | 0.50 |
| *Staph. epidermidis* ATCC 155-1 | 1.0 | 0.25 | 0.25 | 0.25 | 0.25 | 0.12 | ≦0.03 | ≦0.03 | ≦0.03 | 0.12 | 0.12 | 0.50 |
| *Ps. aeruginosa* ATCC 9721 | 0.5 | 2.00 | 2.00 | 2.00 | 2.00 | 0.50 | 0.25 | 0.50 | 0.50 | 0.25 | 2.00 | 2.00 |
| *Ps. aeruginosa* ATCC 10145 | 1.0 | 2.00 | 4.00 | 2.00 | 4.0 | 1.00 | 0.50 | 1.00 | 0.50 | 0.50 | 2.00 | 2.00 |
| *Citr. freundii* ATCC 11606 | 0.25 | 0.25 | 0.12 | 0.12 | 0.25 | 0.12 | 0.06 | 0.06 | ≦0.03 | ≦0.03 | 0.12 | 0.50 |
| *Morg. morganii* ATCC 8019 | 0.12 | 0.25 | 0.50 | 0.25 | 0.25 | 0.12 | 0.06 | 0.06 | 0.06 | ≦0.03 | 0.12 | 0.50 |
| *Proteus vulgaris* ATCC 8427 | 0.06 | 0.50 | 0.50 | 0.25 | 0.50 | 0.12 | 0.06 | 0.12 | 0.06 | 0.06 | 0.25 | 1.00 |
| *Kleb. pneumoniae* ATCC 10031 | 0.03 | 0.06 | ≦0.03 | ≦0.03 | 0.06 | ≦0.03 | ≦0.03 | ≦0.03 | ≦0.03 | ≦0.03 | ≦0.03 | 0.06 |
| *Sal. typhimurium* ATCC 14028 | 0.25 | 0.50 | 0.50 | 0.25 | 0.25 | 0.06 | ≦0.03 | ≦0.03 | 0.06 | ≦0.03 | 0.12 | 0.50 |
| *Sal. typhi* ATCC 6539 | 0.06 | 0.25 | 0.25 | 0.25 | 0.25 | 0.06 | ≦0.03 | ≦0.03 | ≦0.03 | ≦0.03 | 0.06 | 0.25 |
| *Escherichia coli* ATCC 10799 | 0.25 | 0.50 | 0.25 | 0.25 | 0.50 | 0.12 | 0.06 | 0.06 | 0.06 | ≦0.03 | 0.12 | 0.50 |
| *Escherichia coli* ATCC 23559 | 0.06 | 0.25 | 0.25 | 0.25 | 0.25 | ≦0.03 | ≦0.03 | ≦0.03 | ≦0.03 | ≦0.03 | 0.06 | 0.25 |
| *Ent. aerogenes* ATCC 15038 | 0.25 | 0.25 | 0.25 | 0.25 | 0.25 | 0.12 | 0.06 | 0.06 | ≦0.03 | ≦0.03 | 0.12 | 0.50 |
| *Ent. cloacae* ATCC 23355 | 0.06 | 0.12 | 0.12 | 0.12 | 0.50 | ≦0.03 | ≦0.03 | ≦0.03 | ≦0.03 | ≦0.03 | 0.06 | 0.25 |
| *Serr. marcescens* ATCC 13880 | 0.50 | 0.50 | 0.50 | 0.50 | 1.00 | 0.25 | 0.12 | 0.12 | 0.25 | 0.06 | 0.25 | 0.50 |
| *Shigella flexnerii* ATCC 12022 | 0.12 | 0.12 | 0.06 | 0.06 | 0.12 | ≦0.03 | ≦0.03 | ≦0.03 | ≦0.03 | ≦0.03 | 0.06 | 0.12 |

-continued

| MICROORGANISM | Norfloxacin | EXAMPLES | | | | | | | | | | |
|---|---|---|---|---|---|---|---|---|---|---|---|---|
| | | 86 | 87 | 88 | 89 | 90 | 91 | 92 | 93 | 94 | 95 | 96 |
| Bacillus subtilis ATCC 6633 | 0.25 | 0.06 | 0.06 | 0.06 | 0.06 | ≦0.03 | ≦0.03 | 0.06 | ≦0.03 | ≦0.03 | 0.06 | 0.06 |
| Bacillus cereus ATCC 11778 | 1.0 | 0.12 | 0.25 | 0.06 | 0.25 | 0.06 | ≦0.03 | 0.06 | ≦0.03 | 0.06 | 0.25 | 0.25 |
| Strep. faecalis ATCC 10541 | 1.0 | 0.50 | 1.00 | 2.00 | 0.50 | 0.25 | 0.06 | 0.25 | 0.50 | 0.25 | 0.50 | 1.00 |
| Staph. aureus ATCC 25178 | 2.0 | 0.12 | 0.12 | 0.12 | 0.25 | 0.06 | ≦0.03 | 0.06 | 0.12 | 0.12 | 0.12 | 0.12 |
| Staph. epidermidis ATCC 155-1 | 1.0 | 0.12 | 0.25 | 0.12 | 0.25 | 0.06 | ≦0.03 | 0.06 | 0.06 | 0.06 | 0.12 | 0.12 |
| Ps. aeruginosa ATCC 9721 | 0.5 | 0.50 | 1.00 | 1.00 | 2.00 | 0.25 | 0.06 | 0.25 | 1.00 | 1.00 | 0.50 | 1.00 |
| Ps. aeruginosa ATCC 10145 | 1.0 | 1.00 | 1.00 | 2.00 | 2.00 | 0.50 | 0.12 | 0.25 | 0.50 | 0.50 | 1.00 | 1.00 |
| Citr. freundii ATCC 11606 | 0.25 | 0.12 | 0.25 | 0.12 | 0.25 | ≦0.03 | ≦0.03 | ≦0.03 | 0.06 | 0.12 | ≦0.03 | 0.06 |
| Morg. morganii ATCC 8019 | 0.12 | 0.25 | 0.25 | 0.25 | 0.25 | ≦0.03 | ≦0.03 | ≦0.03 | 0.25 | 0.25 | ≦0.03 | 0.06 |
| Proteus vulgaris ATCC 8427 | 0.06 | 0.50 | 1.00 | 0.50 | 0.25 | 0.12 | ≦0.03 | 0.25 | 0.25 | 0.12 | 0.25 | 0.25 |
| Kleb. pneumoniae ATCC 10031 | 0.03 | 0.06 | 0.06 | 0.06 | 0.06 | ≦0.03 | ≦0.03 | ≦0.03 | ≦0.03 | ≦0.03 | ≦0.03 | 0.06 |
| Sal. typhimurium ATCC 14028 | 0.25 | 0.25 | 0.25 | 0.12 | 0.25 | ≦0.03 | ≦0.03 | ≦0.03 | 0.12 | 0.25 | 0.06 | 0.06 |
| Sal. typhi ATCC 6539 | 0.06 | 0.12 | 0.12 | 0.06 | 0.25 | ≦0.03 | ≦0.03 | ≦0.03 | 0.06 | 0.12 | 0.06 | 0.06 |
| Escherichia coli ATCC 10799 | 0.25 | 0.25 | 0.25 | 0.25 | 0.25 | ≦0.03 | ≦0.03 | ≦0.03 | ≦0.03 | ≦0.03 | ≦0.03 | 0.06 |
| Escherichia coli ATCC 23559 | 0.06 | 0.12 | 0.12 | 0.12 | 0.12 | ≦0.03 | ≦0.03 | ≦0.03 | ≦0.03 | ≦0.03 | ≦0.03 | 0.06 |
| Ent. aerogenes ATCC 15038 | 0.25 | 0.25 | 0.12 | 0.12 | 0.25 | ≦0.03 | ≦0.03 | ≦0.03 | 0.06 | 0.12 | 0.06 | 0.06 |
| Ent. cloacae ATCC 23355 | 0.06 | 0.12 | 0.12 | 0.12 | 0.25 | ≦0.03 | ≦0.03 | ≦0.03 | 0.06 | 0.12 | ≦0.03 | 0.06 |
| Serr. marcescens ATCC 13880 | 0.50 | 0.50 | 0.25 | 0.25 | 0.50 | ≦0.03 | ≦0.03 | 0.25 | 1.00 | 1.00 | 0.25 | 0.50 |
| Shigella flexnerii ATCC 12022 | 0.12 | 0.06 | 0.12 | 0.06 | 0.06 | 0.06 | 0.06 | ≦0.03 | ≦0.03 | ≦0.03 | ≦0.03 | 0.06 |

| MICROORGANISM | Norfloxacin | EXAMPLES | | | | | | | | | | |
|---|---|---|---|---|---|---|---|---|---|---|---|---|
| | | 97 | 98 | 99 | 100 | 101 | 102 | 103 | 104 | 105 | 106 | 107 |
| Bacillus subtilis ATCC 6633 | 0.25 | 0.06 | 0.06 | 0.12 | 0.25 | 0.06 | 0.06 | 0.12 | 0.12 | 0.25 | 0.25 | 0.06 |
| Bacillus cereus ATCC 11778 | 1.0 | 0.50 | 0.25 | 0.25 | 0.25 | 0.25 | 0.25 | 0.25 | 0.25 | 0.25 | 0.25 | 0.25 |
| Strep. faecalis ATCC 10541 | 1.0 | 1.00 | 1.00 | 2.00 | 2.00 | 0.50 | 1.00 | 1.00 | 1.00 | 2.00 | 2.00 | 1.00 |
| Staph. aureus ATCC 25178 | 2.0 | 0.12 | 0.12 | 0.25 | 0.25 | 0.12 | 0.12 | 0.25 | 0.25 | 0.25 | 0.25 | 0.12 |
| Staph. epidermidis ATCC 155-1 | 1.0 | 0.12 | 0.12 | 0.12 | 0.25 | 0.12 | 0.12 | 0.12 | 0.25 | 0.25 | 0.25 | 0.25 |
| Ps. aeruginosa ATCC 9721 | 0.5 | 1.00 | 1.00 | 2.00 | 2.00 | 0.50 | 1.00 | 1.00 | 1.00 | 2.00 | 2.00 | 1.00 |
| Ps. aeruginosa ATCC 10145 | 1.0 | 1.00 | 1.00 | 2.00 | 2.00 | 1.00 | 1.00 | 1.00 | 1.00 | 2.00 | 2.00 | 1.00 |
| Citr. freundii ATCC 11606 | 0.25 | 0.12 | 0.12 | 0.12 | 0.12 | ≦0.03 | 0.03 | 0.06 | 0.06 | 0.12 | 0.12 | 0.25 |
| Morg. morganii ATCC 8019 | 0.12 | 0.06 | 0.06 | 0.25 | 0.25 | 0.12 | 0.03 | 0.06 | 0.12 | 0.25 | 0.25 | 0.25 |
| Proteus vulgaris ATCC 8427 | 0.06 | 0.25 | 0.25 | 0.50 | 0.50 | 0.25 | 0.25 | 0.25 | 0.25 | 0.50 | 0.50 | 1.00 |
| Kleb. pneumoniae ATCC 10031 | 0.03 | 0.12 | 0.12 | 0.12 | 0.12 | ≦0.03 | 0.03 | 0.03 | 0.06 | 0.12 | 0.12 | 0.06 |
| Sal. typhimurium ATCC 14028 | 0.25 | 0.06 | 0.06 | 0.25 | 0.25 | 0.06 | 0.06 | 0.06 | 0.06 | 0.25 | 0.25 | 0.25 |
| Sal. typhi ATCC 6539 | 0.06 | 0.06 | 0.12 | 0.12 | 0.12 | 0.06 | 0.06 | 0.12 | 0.12 | 0.25 | 0.25 | 0.12 |
| Escherichia coli ATCC 10799 | 0.25 | 0.06 | 0.06 | 0.12 | 0.12 | ≦0.03 | ≦0.03 | ≦0.03 | ≦0.03 | 0.12 | 0.12 | 0.25 |
| Escherichia coli ATCC 23559 | 0.06 | 0.06 | 0.06 | 0.12 | 0.12 | ≦0.03 | ≦0.03 | ≦0.03 | ≦0.03 | 0.12 | 0.12 | 0.12 |
| Ent. aerogenes ATCC 15038 | 0.25 | 0.12 | 0.12 | 0.12 | 0.12 | 0.06 | 0.06 | 0.06 | 0.06 | 0.12 | 0.12 | 0.12 |
| Ent. cloacae ATCC 23355 | 0.06 | 0.06 | 0.06 | 0.12 | 0.12 | ≦0.03 | ≦0.03 | 0.06 | 0.06 | 0.12 | 0.12 | 0.12 |
| Serr. marcescens ATCC 13880 | 0.50 | 0.50 | 0.50 | 0.50 | 0.50 | 0.25 | 0.50 | 0.50 | 0.50 | 0.50 | 0.50 | 0.25 |
| Shigella flexnerii ATCC 12022 | 0.12 | 0.06 | 0.06 | 0.12 | 0.12 | ≦0.03 | ≦0.03 | 0.06 | 0.06 | 0.12 | 0.12 | 0.12 |

-continued

| MICROORGANISM | Norfloxacin | EXAMPLES 108 | 109 | 110 | 111 |
|---|---|---|---|---|---|
| *Bacillus subtilis* ATCC 6633 | 0.25 | 0.06 | ≦0.03 | 0.06 | 0.06 |
| *Bacillus cereus* ATCC 11778 | 1.0 | 0.25 | 0.12 | 0.25 | 0.12 |
| *Strep. faecalis* ATCC 10541 | 1.0 | 1.00 | 0.50 | 0.50 | 1.00 |
| *Staph. aureus* ATCC 25178 | 2.0 | 0.12 | 0.12 | 0.25 | 0.12 |
| *Staph. epidermidis* ATCC 155-1 | 1.0 | 0.25 | 0.12 | 0.25 | 0.12 |
| *Ps. aeruginosa* ATCC 9721 | 0.5 | 1.00 | 1.00 | 2.00 | 1.00 |
| *Ps. aeruginosa* ATCC 10145 | 1.0 | 1.00 | 1.00 | 2.00 | 0.50 |
| *Citr. freundii* ATCC 11606 | 0.25 | 0.25 | 0.12 | 0.25 | 0.06 |
| *Morg. morganii* ATCC 8019 | 0.12 | 0.25 | 0.12 | 0.25 | 0.25 |
| *Proteus vulgaris* ATCC 8427 | 0.06 | 1.00 | 0.25 | 0.25 | 0.50 |
| *Kleb. pneumoniae* ATCC 10031 | 0.03 | 0.06 | ≦0.03 | 0.06 | ≦0.03 |
| *Sal. typhimurium* ATCC 14028 | 0.25 | 0.25 | 0.12 | 0.25 | 0.12 |
| *Sal. typhi* ATCC 6539 | 0.06 | 0.12 | 0.12 | 0.25 | 0.12 |
| *Escherichia coli* ATCC 10799 | 0.25 | 0.25 | 0.06 | 0.25 | 0.06 |
| *Escherichia coli* ATCC 23559 | 0.06 | 0.12 | ≦0.03 | 0.12 | 0.06 |
| *Ent. aerogenes* ATCC 15038 | 0.25 | 0.12 | 0.06 | 0.25 | 0.06 |
| *Ent. cloacae* ATCC 23355 | 0.06 | 0.12 | 0.06 | 0.25 | 0.06 |
| *Serr. marcescens* ATCC 13880 | 0.50 | 0.25 | 0.25 | 0.50 | 0.50 |
| *Shigella flexnerii* ATCC 12022 | 0.12 | 0.12 | ≦0.03 | 0.06 | ≦0.03 |

In human therapy, the dose for administration is naturally dependent on the susceptibility of the infective strain, the nature of the compound administered and the administration route. It will generally be between approximately 0.200 and approximately 300 mg per kilogram of body weight and per day. The derivatives of the invention will, for example, be administered in the form of tablets, solutions or suspensions, or alternatively gelatin capsules.

By way of examples, two particular dosage forms of the derivatives which are the subject of the present invention are shown below.

| Example of formula per tablet | |
|---|---|
| Compound of Example 9 | 250 mg |
| Microcrystalline cellulose | 69 mg |
| Povidone | 15 mg |
| Wheat starch | 36 mg |
| Colloidal silica | 2 mg |
| Magnesium stearate | 3 mg |
| Tablet weight | 375 mg |

| Example of formula per gelatin capsule | |
|---|---|
| Compound of Example 9 | 250 mg |
| Polyoxyethylenated glyceride | 85 mg |
| Glyceryl behenate | 15 mg |
| Excipient: soft gelatin q.s. | 450 mg |

We claim:

1. The compounds which correspond to the formula I

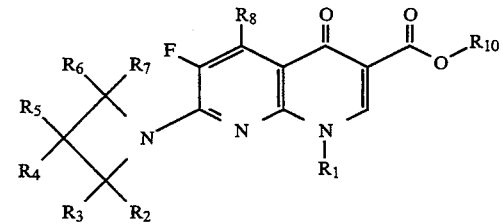

in which $R_1$ represents a lower alkyl radical, a lower haloalkyl radical, an aryl radical or an aryl radical substituted with one or more fluorine atoms(s);

$R_4$ represents an amino radical;

$R_3$, $R_6$ and $R_7$ each represent a hydrogen atom;

$R_2$ and $R_5$ represent a hydrogen atom or a lower alkyl radical, provided that one of $R_2$ and $R_5$ represent a hydrogen atom and the other represents a lower alkyl radical;

$R_8$ represents a hydrogen atom, a nitro radical or an amino radical; and $R_{10}$ represents a hydrogen atom or a $C_1$ to $C_4$ lower alkyl radical;

wherein the azetidine substituents can have, depending on the number, nature and relative position of the substituents, up to three chiral centers, each of them with an "R" or "S" configuration; as well as their physiologically acceptable salts with inorganic acids, or with organic acids.

2. The compounds corresponding to formula I of claim 1 wherein $R_1$ represents an aryl radical substituted with at least one fluorine atom and $R_2$ represents a lower alkyl radical.

3. The compounds corresponding to formula I of claim 1 wherein $R_1$ represents a 2,4-difluorophenyl radical.

4. The compounds corresponding to formula I of claim 1 wherein $R_2$ represents a methyl radical.

5. The compounds corresponding to formula I of claim 1 wherein each of $R_5$, $R_8$, and $R_{10}$ represents a hydrogen atom.

6. The compounds corresponding to the formula I according to claim 1, selected from the following group:
   1-cyclopropyl-6-fluoro-7-(3-amino-3-methyl-1-azetidinyl)-1, 4-dihydro-4-oxo-1, 8-naphthyridine-3-carboxylic acid;
   1-cyclopropyl-6-fluoro-7-(trans-3-amino-2-methyl-1-azetidinyl)-1, 4-dihydro-4-oxo-1, 8-naphthyridine-3-carboxylic acid;
   (−)-1-cyclopropyl-6-fluoro-7-[(2R, 3S)-3-amino-2-methyl-1-azetidinyl]-1, 4-dihydro-4-oxo-1, 8-naphthyridine-3-carboxylic acid;
   (+)-1-cyclopropyl-6-fluoro-7-[(2S, 3R)-3-amino-2-methyl-1-azetidinyl]-1, 4-dihydro-4-oxo-1, 8-naphthyridine-3-carboxylic acid;
   1-(1,1-dimethylethyl)-6-fluoro-7-(3-amino-3-methyl-1-azetidinyl)-1, 4-dihydro-4-oxo-1, 8-naphthyridine-3-carboxylic acid;
   7-(trans-3-amino-2-methyl-1-azetidinyl)-6-fluoro-1-(1,1, -dimethylethyl)-1, 4-dihydro-4-oxo-1, 8-naphthyridine-3-carboxylic acid;
   1-(2,4-difluorophenyl)-6-fluoro-7-(3-methyl-3-amino-1-azetidinyl)-1, 4-dihydro-4-oxo-1, 8-naphthyridine-3-carboxylic acid;
   (±)-1-(2,4-difluorophenyl)-6-fluoro-7-(trans-2-methyl-3-amino-1-azetidinyl)-1, 4-dihydro-4-oxo-1, 8-naphthyridine-3-carboxylic acid;
   (±)-6-fluoro-1-(2-fluoroethyl)-7-(trans-2-methyl-3-amino-1-azetidinyl)-1, 4-dihydro-4-oxo-1, 8-naphthyridine-3-carboxylic acid;
   6-fluoro-1-(2-fluoroethyl)-7-(3-methyl-3-amino-1-azetidinyl)-1, 4-dihydro-4-oxo-1, 8-naphthyridine-3-carboxylic acid;
   (±)-1-ethyl-6-fluoro-7-(trans-2-methyl-3-amino-1-azetidinyl)-1, 4-dihydro-4-oxo-1, 8-naphthyridine-3-carboxylic acid;
   1-ethyl-6-fluoro-7-(3-methyl-3-amino-1-azetidinyl)-1, 4-dihydro-4-oxo-1, 8-naphthyridine-3-carboxylic acid;
   (±)-6-fluoro-1-(4-fluorophenyl)-7-(trans-2-methyl-3-amino-1-azetidinyl)-1, 4-dihydro-4-oxo-1, 8-naphthyridine-3-carboxylic acid;
   6-fluoro-1-(4-fluorophenyl)-7-(3-methyl-3-amino-1-azetidinyl)-1, 4-dihydro-4-oxo-1, 8-naphthyridine-3-carboxylic acid.

7. Pharmaceutical compositions, characterized in that they contain, in addition to a pharmaceutically acceptable vehicle, at least one derivative of formula I or one of its physiologically acceptable salts, according to claim 1.

* * * * *